US005948782A

United States Patent [19]
Sohda et al.

[11] Patent Number: 5,948,782

[45] Date of Patent: Sep. 7, 1999

[54] PHARMACEUTICAL COMPOSITION CONTAINING QUINOLINE AND QUINAZOLINE DERIVATIVES AND NOVEL COMPOUNDS THEREFOR

[75] Inventors: Takashi Sohda, Takatsuki; Haruhiko Makino, Inagawa-cho; Atsuo Baba, Ashiya, all of Japan

[73] Assignee: Takeda Chemical, Osaka, Japan

[21] Appl. No.: 08/049,500

[22] Filed: Apr. 21, 1993

[30] Foreign Application Priority Data

| | | | |
|---|---|---|---|
| Apr. 24, 1992 | [JP] | Japan | 4-106424 |
| May 14, 1992 | [JP] | Japan | 4-121887 |
| Oct. 23, 1992 | [JP] | Japan | 4-285865 |
| Feb. 26, 1993 | [JP] | Japan | 4-037952 |

[51] Int. Cl.[6] .......................... A01N 43/54; A01N 43/42; C07D 215/38; C07D 239/72

[52] U.S. Cl. .......................... 514/258; 514/314; 514/269; 514/248; 546/156; 544/283; 544/319; 544/284

[58] Field of Search ............................ 546/156; 514/314, 514/258, 269, 248; 544/283, 319, 284

[56] References Cited

U.S. PATENT DOCUMENTS

| | | | |
|---|---|---|---|
| 5,352,684 | 10/1994 | Zimmerman et al. | 514/299 |

FOREIGN PATENT DOCUMENTS

| | | |
|---|---|---|
| 259687 | 3/1988 | European Pat. Off. . |
| 299727 | 1/1989 | European Pat. Off. . |
| 0304063 | 2/1989 | European Pat. Off. . |
| 0 530 693 A1 | 8/1992 | European Pat. Off. . |
| 0 499 926 A1 | 10/1992 | European Pat. Off. . |
| 0 608 870 A1 | 1/1994 | European Pat. Off. . |
| 2134169 | 4/1971 | France . |
| 3935491 | 5/1991 | Germany . |

OTHER PUBLICATIONS

Chemical Abstracts, 27–Heterocycles, vol. 89, 1978 (89: 179826m).

Chemical Abstracts, vol. 87, 1977 (87: 184455c).

Chemical Abstracts, 28–Heterocycles, vol. 80, 1974 (82872z).

Chemical Abstracts, vol. 111, 1989 (111: 134010x).

Chemical Abstracts, 32–Heterocyclic Compounds, vol. 57, 1962, pp. 829–832.

J. Heterocyclic Chem., vol. 15, p. 687, 1978.

Uff et al., J. Chem. Soc. Perkin Trans. I, (1986) 2295–2303.

Fuhrer et al., J. Org. Chem., 44(7), 1132–6 (1979).

Sliskovic et al., J. Med. Chem., 34, 367–373 (1991).

Azini et al., II Farmaco, 44(6) 555–563 (1989).

Bergman et al., Tetrahedron, 42(13), 3697–3706 (1986).

*Primary Examiner*—Johann Richter
*Assistant Examiner*—Dominic Keating
*Attorney, Agent, or Firm*—Foley & Lardner

[57] ABSTRACT

There is disclosed an anti-inflammatory agent comprising a compound of the formula (I):

(I)

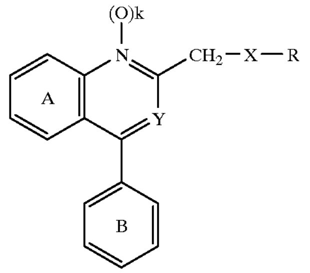

The quinoline compounds included in the compound (I) are novel and there is also disclosed processes for producing them.

74 Claims, No Drawings

PHARMACEUTICAL COMPOSITION CONTAINING QUINOLINE AND QUINAZOLINE DERIVATIVES AND NOVEL COMPOUNDS THEREFOR

FIELD OF THE INVENTION

The present invention relates to an anti-inflammatory agent, particularly agent for treating arthritis, containing a quinoline or quinazoline derivative and to novel quinoline derivatives or salts thereof useful as an anti-inflammatory agent.

BACKGROUND OF THE INVENTION

Arthritis is an inflammatory disease of arthroses. As main examples of arthritis, there are rheumatoid arthritis and its analogous diseases wherein inflammation is observed in arthroses.

Among them, rheumatoid arthritis, also referred to as chronic rheumatism, is polyarthritis chronica whose main lesion is inflammatory changes in synovial membrane of internal layers of articular capsules. Arthritis such as rheumatoid arthritis is progressive and causes articular disorders such as articular deformation, tetany or the like. When an effective treatment is not carried out and the disease worsens, serious physical disorders are often caused.

Hitherto, in treatment of such arthritis, chemotherapy has been carried out using steroids such as adrenal cortical hormones (e.g., cortisone, etc.) or the like; non-steroidal anti-inflammatory agents such as aspirin, piroxicam, indometacin or the like; gold preparations such as gold thiomalate or the like; antirheumatic agents such as chloroquine preparations, D-penicillamine or the like; antipodagrics such as colchicine or the like; immunosuppressive agents such as cyclophosphamide, azathioprine, methotrexate, levamisole or the like; or the like.

However, drugs using the chemotherapy have problems such as serious side effects, side effects making their long-term use difficult, insufficient efficacy, inefficacy against arthritis which has already produced the symptoms.

Therefore, in clinical treatment of arthritis, drugs having low toxicity and excellent effects in the prophylaxis and treatment of arthritis have been required.

OBJECTS OF THE INVENTION

One object of the present invention is to provide a novel anti-inflammatory agent comprising a quinoline or quinazoline derivative.

Another object of the present invention is to provide novel quinoline or quinazoline derivatives useful as an anti-inflammatory agent.

Further, another object of the present invention is to provide processes for producing the above quinoline or quinazoline derivatives.

These objects as well as other objects and advantages of the present invention will become apparent to those skilled in the art from the following description.

SUMMARY OF THE INVENTION

The present inventors have found that quinoline or quinazoline derivatives to which an optionally oxidized sulfur atom, oxygen atom or alkylene group is attached to their 2-positions through a methylene group have anti-arthritic activity, anti-inflammatory activity, antipyretic and analgesic activity, anti-IL-1 activity, antigen-responsive T cell growth inhibitory activity and the like and are useful as anti-inflammatory agents. Thus, the present invention has been completed.

That is, according to the present invention, there is provided:

(1) An anti-inflammatory agent comprising a compound of the formula (I):

(I)

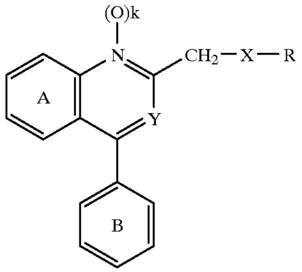

wherein Y is a nitrogen atom or C—G (wherein G is carboxyl which may be esterified); X is an optionally oxidized sulfur atom, oxygen atom or $-(CH_2)_q-$ (wherein q is an integer of 1 to 5); R is an optionally substituted hydrocarbon group or optionally substituted heterocyclic group having a ring-constituting carbon atom attached to X; each of A ring and B ring may optionally have at least one substituent; and k is 0 or 1, or a salt thereof;

(2) A compound of the formula (I'):

(I')

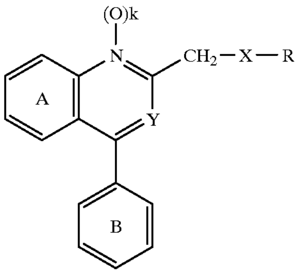

wherein Y is C—G (wherein G is carboxyl which may be esterified); X is an optionally oxidized sulfur atom or $-(CH_2)_q-$ (wherein q is an integer of 1 to 5); R is an optionally substituted hydrocarbon group or optionally substituted heterocyclic group having a ring-constituting carbon atom attached to X; each of A ring and B ring may optionally have at least one substituent; and k is 0 or 1, or a salt thereof;

(3) A process for producing a compound of the formula (I-1):

(I-1)

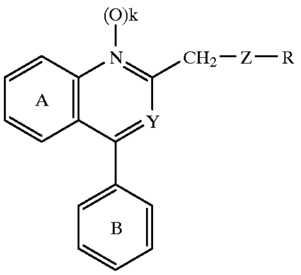

wherein Y is C—G (wherein G is carboxyl which may be esterified); Z is an optionally oxidized sulfur atom; R is an optionally substituted hydrocarbon group or optionally substituted heterocyclic group having a ring-constituting carbon atom attached to Z; each of A ring and B ring may optionally have at least one substituent; and k is 0 or 1, or a salt thereof, which comprises reacting a compound of the formula (II):

(II)

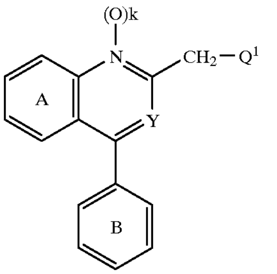

wherein $Q^1$ is a leaving group; Y is C—G (wherein G is carboxyl which may be esterified); each of A ring and B ring may optionally have at least one substituent; and k is 0 or 1, or a salt thereof with a compound of the formula (III):

R—SH (III)

wherein R is an optionally substituted hydrocarbon atom or optionally substituted heterocyclic group having a ring-constituting carbon atom attached to the sulfur atom, and, if necessary, subjecting the resultant to oxidation; and (4) A process for producing a compound of the formula (I-2):

(I-2)

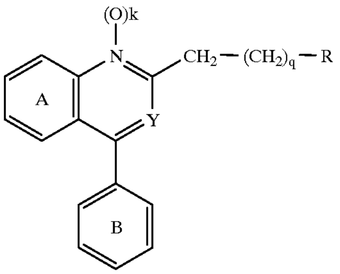

wherein Y is C—G (wherein G is carboxyl which may be esterified); R is an optionally substituted hydrocarbon group or optionally substituted heterocyclic group having a ring-constituting carbon atom attached to $—(CH_2)_q—$ (wherein q is an integer of 1 to 5); each of A ring and B ring may optionally have at least one substituent; and k is 0 or 1, or a salt thereof, which comprises reacting a compound of the formula (IV):

(IV)

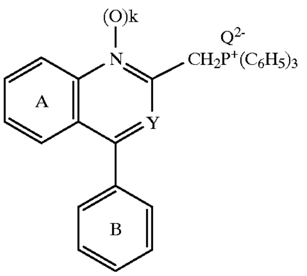

wherein Y is C—G (wherein G is carboxyl which may be esterified); $Q^2$ is a halogen atom; each of A ring and B ring may optionally have at least one substituent; and k is 0 or 1, with the compound of the formula (V):

$R—(CH_2)_{q-1}—CHO$ (V)

wherein R is an optionally substituted hydrocarbon group or optionally substituted heterocyclic group having a ring-constituting carbon atom attached to $—(CH_2)_{q-1}—$ (wherein q is an integer of 1 to 5), and subjecting the resultant to reduction.

DETAILED DESCRIPTION OF THE INVENTION

As examples of the hydrocarbon group represented by R in the formulas (I), (I'), (I-1), (I-2), (III) and (V), there are aliphatic chain hydrocarbon groups, aliphatic cyclic hydrocarbon groups, aromatic hydrocarbon groups and the like.

The aliphatic chain hydrocarbon groups include straight-chain or branched-chain aliphatic hydrocarbon groups such as alkyl, preferably $C_{1-10}$ alkyl, alkenyl, preferably $C_{2-10}$ alkenyl, $C_{2-10}$ alkynyl and the like.

Preferred examples of the alkyl include methyl, ethyl, propyl, isopropyl, butyl, isobutyl, sec-butyl, tert-butyl, pentyl, isopentyl, neopentyl, tert-pentyl, 1-ethyl-propyl, hexyl, isohexyl, 1,1-dimethylbutyl, 2,2-dimethyl-butyl, 3,3-dimethylbutyl, 2-ethylbutyl, hexyl, heptyl, octyl, nonyl, decyl and the like.

Preferred examples of the alkenyl include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Preferred examples of the alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

The aliphatic cyclic hydrocarbon groups include saturated or unsaturated aliphatic cyclic hydrocarbon groups such as cycloalkyl, cycloalkenyl, cycloalkadienyl and the like.

Preferred examples of the cycloalkyl include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferred examples of the cycloalkenyl include 2-cyclopenten-1-yl, 3-cyclopenten-1-yl, 2-cyclohexen-1-yl, 3-cyclohexen-1-yl and the like.

Preferred examples of the cycloalkadienyl include 2,4-cyclopentadien-1-yl, 2,4-cyclohexadien-1-yl, 2,5-cyclohexadien-1-yl and the like.

The aromatic hydrocarbon groups include monocyclic or condensed polycyclic aromatic hydrocarbon groups. Preferable examples thereof include $C_{6-14}$ aryl such as phenyl, naphtyl, anthryl, phenanthryl, acenaphthylenyl and the like. Among them, phenyl, 1-naphtyl, 2-naphtyl and the like are preferred.

The heterocyclic group represented by R in the formulas (I), (I'), (I-1), (I-2), (III) and (V) means an aromatic heterocyclic group, or a saturated or unsaturated non-aromatic heterocyclic group (aliphatic heterocyclic group) each of which has at least one hetero atoms selected from oxygen, sulfur and nitrogen as an atom constituting the ring system (ring-constituting atom). The heterocyclic group is attached to a group defined as X above through its ring-constituting carbon atom.

The aromatic heterocyclic group includes aromatic monocyclic heterocyclic groups, aromatic condensed heterocyclic groups and the like.

Preferred examples of the aromatic monocyclic heterocyclic groups include furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like.

Preferred examples of the aromatic condensed heterocyclic groups include benzofuranyl, isobenzofuranyl, benzo[b]thienyl, indolyl, isoindolyl, 1H-indazolyl, benzoimidazolyl, benzoxazolyl, 1,2-benzisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

Preferred examples of the non-aromatic heterocyclic groups include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like.

Each of the above aliphatic chain hydrocarbon groups, aliphatic cyclic hydrocarbon groups, aromatic hydrocarbon groups, heterocyclic groups and the like may have at least one, preferably 1 to 3 appropriate substituents.

Examples of the substituents include $C_{1-6}$ alkyl, $C_{2-6}$ alkenyl, $C_{2-6}$ alkynyl, cycloalkyl, aryl, aromatic heterocyclic groups, non-aromatic heterocyclic groups, aralkyl, amino, N-monosubstituted amino, N,N-disubstituted amino, amidino, acyl, carbamoyl, N-monosubstituted carbamoyl, N,N-disubstituted carbamoyl, sulfamoyl, N-monosubstituted sulfamoyl, N,N-disubstituted sulfamoyl, carboxyl, lower alkoxycarbonyl having $C_{1-6}$ alkoxy, hydroxyl, $C_{1-6}$ alkoxy, $C_{2-6}$ alkenyloxy, cycloalkyloxy, aralkyloxy, aryloxy, mercapto, $C_{1-6}$ alkylthio, aralkylthio, arylthio, sulfo, cyano, azido, nitro, nitroso, halogen and the like.

When the compound of the formula (I), (I'), (I-1), (I-2), (II) or (IV) is a quinoline derivative, namely when Y represents C—G, examples of the esterified carboxyl represented by G include alkyloxycarbonyl and aralkyloxycarbonyl.

Examples of the alkyl in the alkyloxycarbonyl include $C_{1-6}$ alkyl such as methyl, ethyl, propyl, isopropyl, butyl, isobutyl, sec-butyl, tert-butyl and the like.

The aralkyl in the aralkyloxycarbonyl means alkyl having aryl as a substituent (arylalkyl). Examples of the aryl include phenyl, naphthyl and the like. The aryl may have the same substituent as that of the aryl represented by R. As the alkyl, $C_{1-6}$ alkyl is preferable. Preferred examples of the aralkyl include benzyl, phenethyl, 3-phenylpropyl, (1-naphthyl)methyl, (2-naphthyl)methyl and the like. Among them, benzyl, phenethyl and the like are more preferred.

The optionally oxidized sulfur atom represented by X and Z includes thio, sulfinyl and sulfonyl.

Examples of the leaving group represented by $Q^1$ in the formula (II) include halogen, preferably chlorine, bromine or iodine; hydroxyl activated by esterification such as organic sulfonic acid residues (e.g., p-toluenesulfonyloxy, methanesulfonyloxy, etc.) and organic phosphoric acid residues (e.g., diphenylphosphoryloxy, dibenzylphosphoryloxy, dimethylphosphoryloxy, etc.); and the like.

Examples of the halogen atom represented by $Q^2$ in the formula (IV) include chlorine, bromine and iodine.

The ring A and ring B in the (I), (I'), (I-1), (I-2), (II) and (IV) may have one or more substituents. Examples of the substituent include halogen, nitro, optionally substituted alkyl, optionally substituted hydroxyl, optionally substituted thiol, optionally substituted amino, optionally substituted acyl, optionally esterified carboxyl and optionally substituted aromatic cyclic groups.

Examples of the halogen as the substituent include fluorine, chlorine, bromine and iodine. In particular, fluorine and chlorine are preferred.

The optionally substituted alkyl may be any of straight-chain, branched-chain or cyclic $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl, cycloheptyl or the like.

As examples of the optionally substituted hydroxyl, there are hydroxyl, hydroxyl having an appropriate substituent, particularly a group used as a protecting group for hydroxyl, such as alkoxy, alkenyloxy, aralkyloxy, acyloxy, aryloxy and the like.

Examples of the alkoxy include $C_{1-10}$ alkoxy such as methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy, cyclohexyloxy and the like.

Examples of the alkenyloxy include $C_{1-10}$ alkenyloxy such as allyloxy, crotyloxy, 2-pentenyloxy, 3-hexenyloxy, 2-cyclopentenylmethoxy, 2-cyclohexenylmethoxy and the like. Examples of the aralkyloxy include phenyl-$C_{1-4}$ alkyloxy such as benzyloxy, phenethyloxy and the like.

Preferred examples of the acyloxy include $C_{2-4}$ alkanoyloxy such as acetyloxy, propionyloxy, n-butyryloxy, isobutyryloxy and the like. Examples of the aryloxy include phenoxy, 4-chlorophenoxy and the like.

As examples of the optionally substituted thiol, there are thiol, thiol having an appropriate substituent, particularly a group used as a protecting group for thiol, such as alkylthio, aralkylthio, acylthio and the like.

Preferred examples of the alkylthio include $C_{1-10}$ alkylthio such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio and the like.

Examples of the aralkylthio include phenyl-$C_{1-4}$ alkylthio such as benzylthio, phenethylthio and the like.

Examples of the acylthio include $C_{2-4}$ alkanoylthio such as acetylthio, propionylthio, n-butyrylthio, isobutyrylthio and the like.

As examples of the optionally substituted amino, there are amino having 1 or 2 substituents selected from $C_{1-10}$ alkyl, $C_{2-10}$ alkenyl and an aromatic group, for example, methylamino, dimethylamino, ethylamino, diethylamino, dibutylamino, diallylamino, cyclohexylamino, phenylamino, N-methyl-N-phenylamino and the like.

As examples of the optionally substituted acyl, there are formyl; carbonyl to which $C_{1-10}$ alkyl, $C_{2-10}$ alkenyl or an aromatic group is attached such as acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl or the like.

As examples of the optionally esterified carboxyl, there are carboxyl, alkyloxycarbonyl, aralkyloxycarbonyl and the like. Examples of the alkyl in the alkyloxycarbonyl include $C_{1-6}$ alkyl such as methyl, ethyl, propyl, isopropyl, butyl, isobutyl, sec-butyl, tert-butyl and the like.

The aralkyl in the aralkyloxycarbonyl means alkyl having aryl as a substituent (arylalkyl). Examples of the aryl include phenyl, naphthyl and the like. These groups may have the same substituent as that of the above aromatic cyclic group represented by R. As the alkyl, $C_{1-6}$ alkyl is preferable. Preferable examples of the aralkyl include benzyl, phenethyl, 3-phenylpropyl, (1-naphthylmethyl)methyl, (2-naphthyl)methyl and the like. Among them, benzyl and phenethyl are preferred.

As examples of the optionally substituted aromatic cyclic groups, there are $C_{6-14}$ aromatic hydrocarbon groups such as phenyl, naphthyl, anthryl or the like; aromatic heterocyclic groups such as pyridyl, furyl, thienyl, imidazolyl, thiazolyl or the like.

The substituent of the A ring and B ring may be at any position in each ring and may be the same or different. The number of the substituent is 1 to 4. When the substituents of the ring A or the ring B are adjacent each other, the adjacent substituents may be joined together to form a ring of the formula: $-(CH_2)_m-$ or $-O-(CH_2)_n-O-$ wherein m is an integer of 3 to 5 and n is an integer of 1 to 3. The resulting ring includes 5 to 7 membered rings formed together with carbon atoms of the benzene ring.

Among compounds of the formula (I), compound of the formula (I') are novel.

Preferable examples of the compounds of the formula (I') include:

ethyl 6,7-dimethoxy-4-(3,4-dimethoxyphenyl)-2-[(1-methylimidazol-2-yl)sulfinylmethyl]quinoline-3-carboxylate (Example 2), ethyl 6,7-dimethoxy-4-(4-methylphenyl)-2-[(1-methylimidazol-2-yl)thiomethyl]quinoline-3-carboxylate (Example 33), ethyl 6,7-dimethoxy-4-(3,4-dimethoxyphenyl)-2-[(4-methyl-1,2,4-triazol-3-yl)thiomethyl]quinoline-3-carboxylate (Example 35), ethyl 6,7-dimethoxy-4-(3,4-dimethoxyphenyl)-2-[(1-methylimidazol-2-yl)thiomethyl]quinoline-3-carboxylate (Example 36), ethyl 6,7-dimethoxy-4-(3,4-methylenedioxyphenyl)-2-[(1-methylimidazol-2-yl)thiomethyl]quinoline-3-carboxylate (Example 69), ethyl 6,7-diethoxy-4-(3,4-dimethoxyphenyl)-2-[(1-methylimidazol-2-yl)thiomethyl]quinoline-3-carboxylate (Example 72), ethyl 6,7-dimethoxy-4-(3,4-dimethoxyphenyl)-2-[2-(1-methylimidazol-2-yl)ethyl]quinoline-3-carboxylate (Example 87), ethyl 2-[(2-benzimidazolyl)sulfinylmethyl]-6,7-dimethoxy-4-(3,4-dimethoxyphenyl)quinoline-3-carboxylate (Example 3), ethyl 6,7-dimethoxy-4-(3,4-dimethoxyphenyl)-2-[(5-fluorobenzimidazol-2-yl)thiomethyl]quinoline-3-carboxylate (Example 54), ethyl 6,7-dimethoxy-4-(3,4-dimethoxyphenyl)-2-[(benzothiazol-2-yl)thiomethyl]quinoline-3-carboxylate (Example 60), ethyl 6,7-dimethoxy-4-(3,4-dimethoxyphenyl)-2- [(3,4-dihydro-4-oxoquinazolin-2-yl)thiomethyl]quinoline-3- carboxylate (Example 64), ethyl 6,7-dimethoxy-4-(4-methoxyphenyl)-2-[(benzimidazol-2-yl)thiomethyl]quinoline-3-carboxylate (Example 27), ethyl 6,7-dimethoxy-4-(4-methoxyphenyl)-2-[(1-methylimidazol-2-yl)thiomethyl]quinoline-3-carboxylate (Example 28), ethyl 6,7-dimethoxy-4-(3,4-dimethoxyphenyl)-2-[(4-chlorophenyl)thiomethyl]quinoline-3-carboxylate (Example 42), ethyl 6,7-dimethoxy-4-(3,4-dimethoxyphenyl)-2-[(pyrido[1,2-a][1,3,4]triazol-5-yl)thiomethyl]quinoline-3-carboxylate (Example 66), ethyl 6,7-dimethoxy-4-(3,4-dimethoxyphenyl)-2-[(4-chlorophenyl)methylthiomethyl]quinoline-3-carboxylate (Example 41), ethyl 6,7-dimethoxy-4-(3,4-dimethoxyphenyl)-2-[(benzimidazol-2-yl)thiomethyl]quinoline-3-carboxylate (Example 53), ethyl 6,7-dimethoxy-4-(3,4-dimethoxyphenyl)-2- [(6(1H)-pyrimidon-2-yl)thiomethyl]quinoline-3-carboxylate (Example 45), ethyl 6,7-dimethoxy-4-(3,4-dimethoxyphenyl)-2-[(3-hydroxypyridin-2-yl)thiomethyl]quinoline-3-carboxylate (Example 46) or ethyl 6,7-dimethoxy-4-(3,4-dimethoxyphenyl)-2-[(2-thiazolin-2-yl)thiomethyl]quinoline-3-carboxylate (Example 47).

The example number in the parentheses is that disclosed hereinafter.

The most preferred example of the compound (I') is ethyl 6,7-dimethoxy-4-(3,4-dimethoxyphenyl)-2-[2-(1-methyl-imidazol-2-yl)ethyl]quinoline-3-carboxylate.

The salts of the desired compound (I) of the present invention are preferably pharmaceutically acceptable salts such as salts with inorganic bases, salts with organic bases, salts with inorganic acids, salts with organic acids, salts with basic or acidic amino acids, or the like.

Preferred examples of the salts with inorganic bases include salts with alkaline metals such as sodium, potassium or the like; salts with alkaline earth metals such as calcium, magnesium or the like; salts with aluminum; ammonium salts; and the like.

Preferred examples of the salts with organic bases include salts with trimethylamine, triethylamine, pyridine, picoline, ethanolamine, diethanolamine, triethanolamine, dicyclohexylamine, N,N'-dibenzylethylenediamine or the like.

Preferred examples of the salts with inorganic acids include salts with hydrochloric acid, hydrobromic acid, nitric acid, sulfuric acid, phosphoric acid or the like.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid or the like.

Preferred examples of the salts with basic amino acids include salts with arginine, lysine, ornithine or the like. Preferred examples of the salts with acidic amino acids include salts with aspartic acid, glutamic acid or the like.

The above compound (I) can be prepared, for example, as follows.

Process A

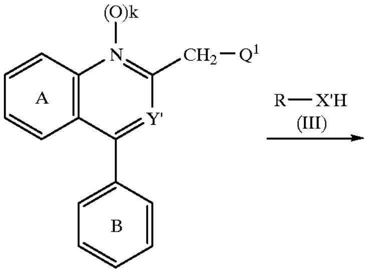

(II)

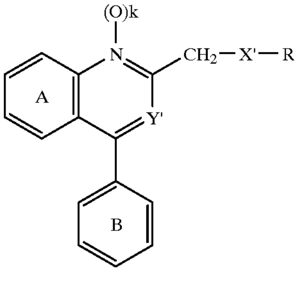

(I-3)

wherein Y' is a nitrogen atom or C—G' (wherein G' is esterified carboxyl) and the other symbols are as defined above.

In this process, the compounds (II) and (III) are reacted in an appropriate solvent in the presence of a base to prepare the compound (I-3).

Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethylsulfoxide, chloroform, dichloromethane, 1,2-dichloroethane, 1,1,2,2-tetrachloroethane, acetone, 2-butanone and mixed solvents thereof.

Examples of the base include alkaline metal salts such as sodium hydroxide, potassium hydroxide, potassium carbonate, sodium carbonate, sodium bicarbonate or the like; silver carbonate ($Ag_2CO_3$); amines such as pyridine, triethylamine, N,N-dimethylaniline or the like. The amount of the base to be used is about 1 to 5 mol per 1 mol of the compound (II).

This reaction is normally carried out at −20° C. to 150° C., preferably −10° C. to 100° C.

The quinoline or quinazoline derivative (I-3) thus obtained can be isolated and purified according to known purification and separation methods such as concentration, concentration under reduced pressure, solvent extraction, crystallization, recrystallization, redistribution, chromatography or the like.

Process B

In this process, the compound (I-4), namely the compound of the formula (I-3) wherein X' is sulfur atom is subjected to oxidation to prepare the compound (I-5).

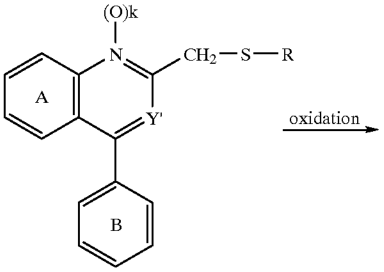

(I-4)

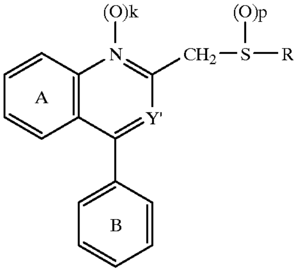

(I-5)

wherein p is 1 or 2 and the other symbols are as defined above.

This oxidation can be carried out according to a conventional manner using an oxidizing agent such as m-chloroperbenzoic acid, hydrogen peroxide, peresters, sodium metaperiodate or the like.

When the oxidizing agent is used in an equimolar amount or less based on the compound (I-4), the compound of the formula (I-5) wherein p is 1 is preferentially produced. The compound of the formula (I-5) wherein p is 2 is produced by oxidation of the compound of the formula (I-5) wherein p is 1 when the oxidizing agent is used in excess of the equimolar amount.

This oxidation is advantageously carried out in a solvent which is inert under reaction conditions such as halogenated hydrocarbons (e.g., methylene chloride, chloroform, dichloroethane, etc.), aromatic hydrocarbons (e.g., benzene, toluene, etc.) and alcohols (e.g., methanol, ethanol, propanol, etc.).

This reaction is carried out at room temperature or lower, preferably about −50° C. to 20° C. normally for 0.5 to 10 hours.

The quinoline or quinazoline derivative (I-5) can be isolated and purified by known separation and purification methods such as concentration, concentration under reduced pressure, solvent extraction, crystallization, recrystallization, redistribution, chromatography or the like.

Process C

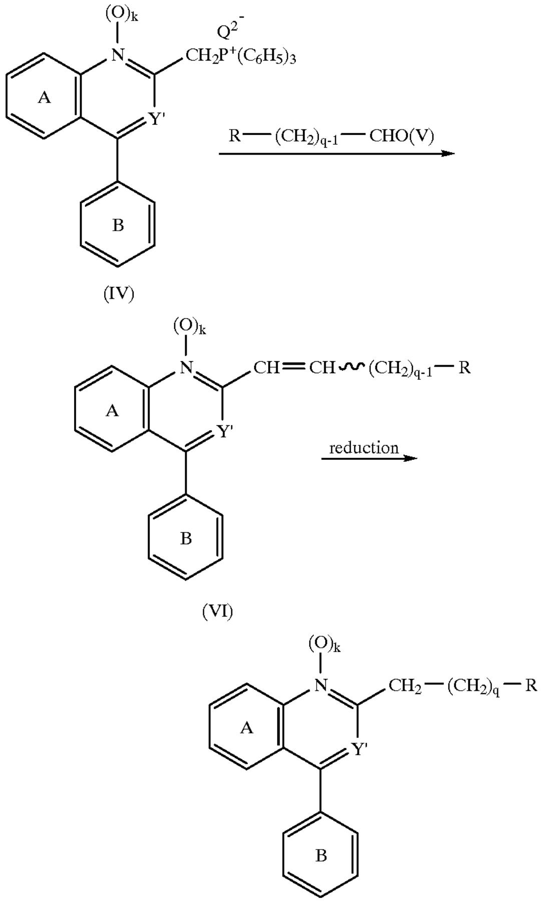

(IV)

(VI)

(I-2)

wherein each symbol is as defined above.

In this process, the aldehyde derivative (V) are condensed with phosphonium salt (IV) to obtain the compound (VI) which is then subjected to reduction to prepare the compound (I-2).

The condensation reaction between the compounds (IV) and (V) is carried out in an appropriate solvent in the presence of a base.

Examples of the solvent include alcohols (e.g., methanol, ethanol, propanol, etc.), ethers (e.g., ethyl ether, dioxane, tetrahydrofuran, dimethoxyethane, etc.), aromatic hydrocarbons (e.g., benzene, toluene, xylene, etc.), dichloromethane, 1,2-dichloroethane, N,N-dimethylformamide, dimethylsulfoxide and mixed solvents thereof.

Examples of the base include alkaline metal hydride (e.g., sodium hydride, potassium hydride, etc.), alkoxides (e.g., sodium ethoxide, sodium methoxide, potassium tert-butoxide, etc.), organic lithium compounds (e.g., methyl lithium, butyl lithium, phenyl lithium, etc.), sodium amide and the like. The amount of the base to be used is preferably about 1 to 1.5 mol per 1 mol of the compound (IV).

This reaction is carried out normally at −50° C. to 100° C., preferably −20° C. to 50° C. The reaction time is 0.5 to 20 hours.

The compound (VI) is obtained as a mixture of (E) and (Z) isomers for the newly formed double bond. After or without separation, the (E) and (Z) isomers each are subjected to reduction to obtain the compound (I-2).

This reduction is carried out according to conventional methods in a solvent in the presence of a catalyst such as palladium catalysts (e.g., palladium carbon, palladium black, etc.), platinum catalysts (e.g., platinum dioxide, etc.), Raney nickel or the like under an atmosphere of hydrogen. Examples of the solvent include alcohols (e.g., methanol, ethanol, propanol, etc.), ethers (e.g., ethyl ether, dioxane, tetrahydrofuran, dimethoxyethane, etc.), aromatic hydrocarbons (e.g., benzene, toluene, xylene, etc.), dichloromethane, 1,2-dichloroethane, ethyl acetate, acetonitrile, acetone, 2-butanone, N,N-dimethylformamide, dimethylsulfoxide, and mixed solvents thereof. The pressure of hydrogen atmosphere is 1 to 150 atm, preferably 1 to 20 atm.

The quinoline or quinazoline derivative (I-2) thus obtained can be isolated and purified by known separation and purification methods such as concentration, concentration under reduced pressure, solvent extraction, crystallization, recrystallization, redistribution, chromatography or the like.

The starting materials (II) and (IV) in the present invention can be prepared, for example, according to the following process.

Process D

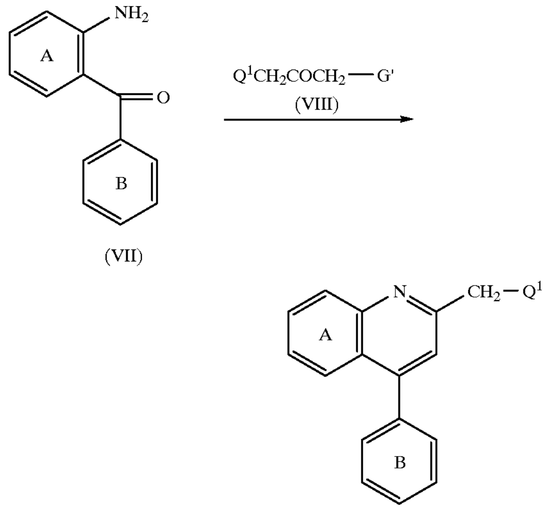

(VII)

(II-1)

wherein each symbol is as defined above.

In this process, the 2-aminobenzophenone derivative (VII) and the compound (VIII) are reacted in an appropriate solvent in the presence of an acid to prepare the compound (II-1).

Examples of the solvent include aromatic hydrocarbons (e.g., benzene, toluene, xylene, etc.), ethers (e.g., dioxane, tetrahydrofuran, dimethoxyethane, etc.), N,N-dimethylformamide, dimethylsulfoxide, chloroform, dichloromethane, 1,2-dichloroethane, 1,1,2,2-tetrachloroethane, acetic acid and the like.

Examples of the acid include Lewis acids (e.g., aluminum chloride, zinc chloride, etc.), p-toluenesulfonic acid, sulfuric acid, trifluoroacetic acid and the like. The amount of the acid to be used is preferably about 0.05 to 0.5 mol per 1 mol of the compound (VII).

This reaction is carried out normally at 20° C. to 200° C., preferably about 30° C. to 150° C. The reaction time is 0.5 to 20 hours, preferably 1 to 10 hours.

The compound (II-1) thus obtained can be isolated and purified by known separation and purification methods such as concentration, concentration under reduced pressure, solvent extraction, crystallization, recrystallization, redistribution, chromatography or the like.

Process E

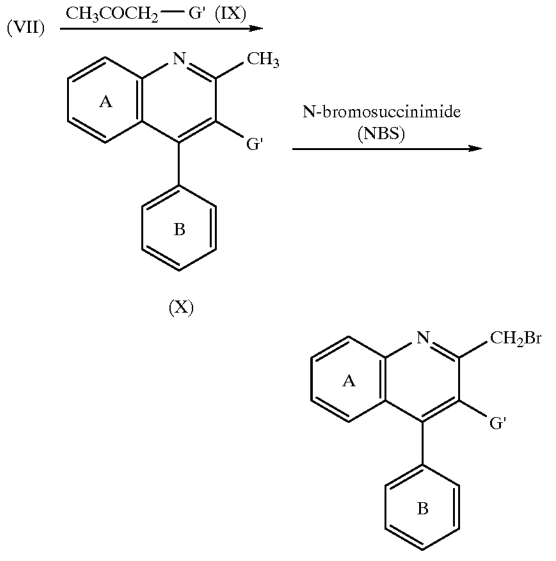

(VII)

(X)

(II-2)

wherein each symbol is as defined above.

In this process, the 2-aminobenzophenone derivative (VII) is reacted with the acetoacetic ester derivative (IX) in the presence of an acid to obtain the compound (X). The compound (X) is then brominated to prepare the 2-bromomethylquinoline derivative (II-2).

The reaction between the compounds (VII) and (IX) can be carried out in the same manner as in the process D.

The bromination of the compound (X) can be carried out in an appropriate solvent in the presence of a free-radical initiator according to conventional methods. Examples of the solvent include halogenated hydrocarbons such as carbon tetrachloride, chloroform, dichloromethane, 1,2-dichloroethane, 1,1,2,2-tetrachloroethane or the like. Examples of the free-radical initiator include benzoyl peroxide, 2,2-azobis(isobutyronitrile) and the like. The amount of the free-radical initiator is preferably about 0.001 to 0.01 mol per 1 mol of the compound (X). This reaction is carried out normally at 20° C. to 150° C., preferably about 30° C. to 100° C. The reaction time is 0.5 to 20 hours, preferably 1 to 10 hours.

The compound (II-2) thus obtained can be isolated and purified by known separation and purification methods such as concentration, concentration under reduced pressure, solvent extraction, crystallization, recrystallization, redistribution, chromatography or the like.

Process F

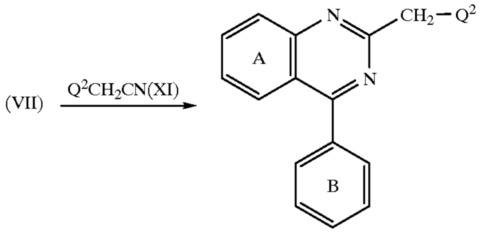

(VII)

(II-3)

wherein each symbol is as defined above.

In this method, the 2-aminobenzophenone derivative (VII) is reacted with the halogenoacetonitrile derivative (XI) to prepare the 2-halogenomethylquinazoline derivative (II-3). The reaction between the compounds (VII) and (XI) is carried out by using an excess amount of the compound (XI) as a solvent in the presence of an acid. As the acid, there can be used the same acids as those described in the process D. The amount of the acid to be used is about 1 to 5 mol, preferably 1 to 2 mol per 1 mol of the compound (VII). The reaction time is normally 0.5 to 30 hours, preferably 1 to 10 hours. The reaction temperature is normally 20° C. to 200° C., preferably 30° C. to 150° C.

The quinazoline derivative (II-3) thus obtained can be isolated and purified by known separation and purification methods such as concentration, concentration under reduced pressure, solvent extraction, crystallization, recrystallization, redistribution, chromatography or the like.

Process G

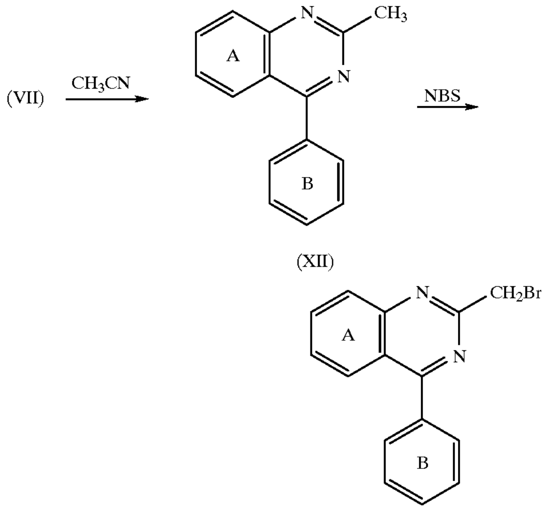

(VII)

(XII)

(II-4)

wherein each symbol is as defined above.

In this process, the 2-aminobenzophenone derivative (VII) is reacted with acetonitrile to prepare the 2-methylquinazoline derivative (XII). The compound (XII) is then subjected to bromination to prepare the 2-bromomethylquinazoline derivative (II-4). The reaction of the compound (VII) with acetonitrile is carried out in the same manner as in the F method. The bromination of the compound (XII) is carried out in the same manner as the bromination of the compound (X) in the process E.

The quinazoline derivative (II-4) can be isolated and purified by known separation and purification methods such as concentration, concentration under reduced pressure, solvent extraction, crystallization, recrystallization, redistribution, chromatography or the like.

Process H

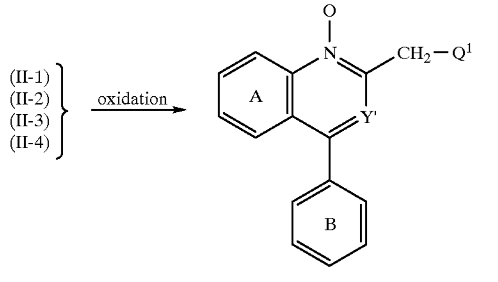

(II-5)

wherein each symbol is as defined above.

In this method, the compounds (II-1), (II-2), (II-3) and (II-4) obtained by the processes D, E, F and G, respectively, are oxidized to prepare the compound (II-5).

This oxidation is carried out according to the same manner using an oxidizing agent such as m-chloroperbenzoic acid, hydrogen peroxide, peresters, sodium metaperiodate or the like. The amount of the oxidizing agent to be used is 1 to 5 mol, preferably 1 to 3 mol per 1 mol of the compound (II-1), (II-2), (II-3) or (II-4).

This oxidation is advantageously carried out in a solvent which is inert under reaction conditions such as halogenated hydrocarbons (e.g., methylene chloride, chloroform, dichloroethane, etc.), aromatic hydrocarbons (e.g., benzene, toluene, etc.) and alcohols (e.g., methanol, ethanol, propanol, etc.).

This reaction is carried out at −10° C. to 150° C., preferably about 0° C. to 100° C. normally for 0.5 to 10 hours.

The quinoline 1-oxide derivative or quinazoline 1-oxide derivative (II-5) thus obtained can be isolated and purified by known separation and purification methods such as concentration, concentration under reduced pressure, solvent extraction, crystallization, recrystallization, redistribution, chromatography or the like.

Process I

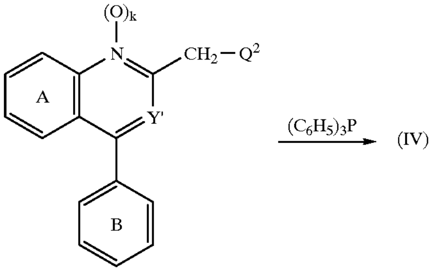

(II-6)

wherein each symbol is as defined above.

In this process, the compound of the formula (II-6) is reacted with the corresponding amount of triphenylphosphine to prepare the phosphonium salt derivative of the formula (IV).

This reaction is carried out in a solvent such as aromatic hydrocarbons (e.g. benzene, toluene, xylene, etc.), ethers (e.g., tetrahydrofuran, dioxane, dimethoxyethane, etc.), acetonitrile and mixed solvents thereof. This reaction is carried out at 10° C. to 200° C., preferably 30° C. to 150° C. for 0.5 to 50 hours.

Process J

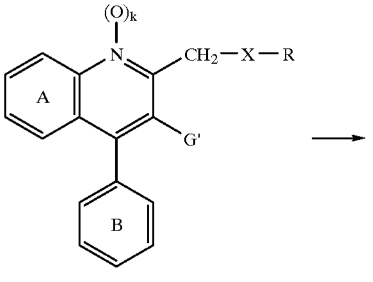

(I-6)

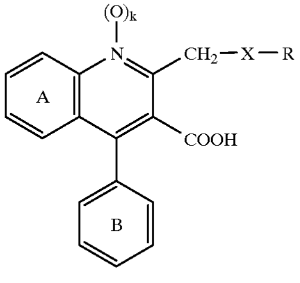

(I-7)

wherein each symbol is as defined above.

In this process, the compound (I-6) is subjected to hydrolysis to prepare the compound (I-7).

The hydrolysis can be carried out in water or in an aqueous solvent according to the conventional methods.

Usable aqueous solvent is a mixture of water and an alcohol (such as methanol or ethanol), an ether (such as tetrahydrofuran or dioxane), N,N-dimethylformamide, dimethylsulfoxide, acetonitrile or acetone.

The reaction is carried out in the presence of a base such as potassium carbonate, sodium carbonate, sodium hydroxide, potassium hydroxide or lithium hydroxide, or an acid such as hydrochloric acid, sulfuric acid, acetic acid or hydrobromic acid. Preferably, the acid or the base is used in an excess amount (base: 1.2 to 6 equivalents; acid: 2 to 50 equivalents) to the compound (Ia'). The reaction is usually conducted at about −20° C. to 150° C., preferably about −10° C. to 100° C.

The compounds and salts thereof provided according to the present invention have anti-inflammatory activity, and antipyretic and analgesic activity. Further, excellent antiarthritic activity was observed in an experimental model of adjuvant arthritis which produces symptoms analogous to those of rheumatoid arthritis in mammals. Furthermore, anti-IL-1 activity and antigen-responsive T cell growth inhibitory activity were observed and these activities suggests action mechanisms of anti-inflammatory activity of the compounds of the present invention.

The compounds of the present invention have low toxicity. For example, when 300 mg/kg of the compounds prepared in Examples 36, 45, 47, 54 and 64 were administered orally to mice, no mice died. Therefore, the compounds of the present invention are useful as an anti-inflammatory agent, particularly an agent for treating arthritis producing inflammatory symptoms, in humans and other mammals.

The compound (I) of the present invention is formulated together with a pharmacologically acceptable carrier and administered orally or parenterally as solid preparations such as tablets, capsules, granules, powders or liquid preparations such as syrups, injections or the like.

As the pharmacologically acceptable carrier, there can be used various organic or inorganic carrier materials conventionally used as pharmaceutical materials. The carriers are formulated as excipients, lubricants, binders or disintegrants in solid preparations; resolvents, solution adjuvants, suspending agents, tonicity agents, buffering agents or soothing agents in liquid preparations; or the like. If necessary, pharmaceutical additives such as antiseptics, antioxidants, colorants, sweetening agents or the like can also be used.

Preferred examples of the excipients include lactose, sucrose, D-mannitol, starch, crystalline cellulose, light silicic anhydride and the like.

Preferred examples of the lubricants include magnesium stearate, calcium stearate, talc, colloidal silica and the like.

Preferred examples of the binders include crystalline cellulose, sucrose, D-mannitol, dextrin, hydroxypropylcellulose, hydroxypropylmethylcellulose, polyvinylpyrrolidone and the like.

Preferred examples of the disintegrants include starch, carboxymethylcellulose, calcium carboxymethylcellulose, croscarmellose sodium, carboxymethylstarch sodium and the like.

Preferred examples of the resolvents in liquid preparations include water for injection, alcohols, propylene glycol, macrogol, sesame oil, corn oil and the like.

Preferred examples of the solution adjuvants include polyethylene glycol, propylene glycol, D-mannitol, benzyl benzoate, ethanol, trisaminomethane, cholesterol, ethanolamine, sodium carbonate, sodium citrate and the like.

Preferred examples of the suspending agents include surfactants such as stearyl triethanolamine, sodium lauryl sulfate, laurylaminopropionic acid, lecithin, banzalkonium chloride, benzethonium chloride, glyceryl monostearate or the like; hydrophilic macromolecules such as polyvinyl alcohol, polyvinyl pyrrolidone, carboxymethylcellulose sodium, methylcellulose, hydroxymethylcellulose, hydroxyethylcellulose, hydroxypropylcellulose or the like.

Preferred examples of the tonicity agents include sodium chloride, glycerin, D-mannitol and the like.

Preferred examples of the buffering agents include phosphates, acetates, carbonates, citrates and the like.

Preferred examples of the soothing agents include benzyl alcohol and the like.

Preferred examples of the antiseptics include paraoxybenzoic esters, chlorobutanol, phenethyl alcohol, dehydroacetic acid, sorbic acid and the like.

Preferred examples of the antioxidants include sulfites, ascorbic acid and the like.

The dose of the compound (I) of the present invention varies widely depending upon a particular route of administration, conditions of a particular patient to be treated or the like. The daily dose for an adult patient can normally be selected from the range of 5 to 1,000 mg for oral administration and 1 to 100 mg for parenteral administration. The compound (I) can be administered in the above daily dose in 1 to 4 divided portions.

Pharmacological activities of the compound (I) or its salt of the present invention can be evaluated by the following Test Examples. The experimental methods and results are shown as follows.

Test Example 1

Effects on Rat Adjuvant Arthritis

Freund's complete adjuvant (a 0.5% suspension of killed tubercule bacilli in liquid paraffin) (0.05 ml) was injected intradermally into a right hind leg plantar of Lewis rats (male, 7 weeks old, Charles River Japan Inc.) for sensitization. A test drug (50 mg/kg) was suspended in 5% acacia and administered once a day for 14 days. The administration was started just before the sensitization (Day 0). The volume of the left hind leg and the body weight were measured just before the sensitization (Day 0) and on the 14th day, and the swelling inhibitory rate (%) and the increase rate (%) of body weight based on drug-unadministered rat groups were calculated.

The results are compared and assessed by Dunnett's test. The risk rate of less than 5% was evaluated as significant. As shown in Table 1, the compound of the present invention was effective in improvement of all symptoms observed as the inhibition of plantar swelling and the increase in body weight.

TABLE 1

| Compound (Example No.) | Swelling inhibitory rate (%) | Increase rate of body weight (%) |
|---|---|---|
| 2 | 73** | 39** |
| 33 | 67** | 12 |
| 36 | 48** | 30** |
| 69 | 63** | 17 |
| 72 | 50** | 27** |
| 35 | 64** | 11 |
| 87 | 75** | 27** |
| 88 | 62** | 24** |

**$p < 0.01$,
*$p < 0.05$

Test Example 2

Rat Carrageenin Paw Edema Inhibitory Activity

The volume of a planter part of a right hind leg of Jcl:SD rats (male, 6 weeks old) was measured, and then suspension of a test drug (50 mg/kg) in 5% acacia was administered orally. Then water was administered additionally so that the total amount of administered liquid became 5 ml/rat. After 1 hour, a suspension (0.05 ml) containing 1% carrageenin in physiological saline was injected intradermally into the plantar to induce swelling [Winter, C. A. et al; Proc. Soc. Exp. Biol. Med., 111, 544 (1962)]. The volume of the right hind leg was measured again 3 hours after the carrageenin injection, and swelling inhibitory rate was calculated from the difference in the volumes before and after the injection.

The results are shown in Table 2. The compound of the present invention exhibited carrageenin paw edema inhibitory activity.

TABLE 2

| Compound (Example No.) | Swelling inhibitory rate (%) |
|---|---|
| 3 | 23 |
| 54 | 21 |
| 60 | 31 |
| 64 | 36 |

Test Example 3

Analgesic Activity in Mice

A drug (50 mg/kg) suspended in 5% acacia was administered orally to Slc:ICR mice (male, 4 weeks old). After 30 minutes, a 0.02% phenylquinone solution (0.1 ml/10 kg body weight) in 5% ethanol was administered intraperitoneally. Writhing and stretching reactions for 20 minutes after the injection were calculated for each mouse to evaluate analgesic activity of the test drug [Siegmund, E. et al.; Proc. Soc. Exp. Biol. Med., 95, 729 (1957)].

The results are shown in Table 3. The compound of the present invention exhibited significant analgesic activity in the mouse phenylquinone writhing model.

TABLE 3

| Compound (Example No.) | Inhibitory rate (%) |
|---|---|
| 27 | 39 |
| 28 | 43 |
| 36 | 59 |
| 42 | 47 |
| 66 | 58 |
| 64 | 27 |

Test Example 4

Anti-IL-1 activity

Rat cartilage cells were prepared according to the known method [Fujio Suzuki et al., Sin Seikagaku Jikken Kohza, 18, p.871–875 (1990)] and cultivated in Dulbecco's Medium containing 10% fetal bovine serum. After 8 days, various concentrations of a test drug and IL-1β (0.2 ng/ml) were added, and the cells were cultivated for additional 3 days. The amount of extracellular substrates thus produced was determined.

The results are shown in Table 4. Although IL-1β inhibits the synthesis of extracellular substrates of cartilage cells, addition of the drug inhibits the IL-1 activity and the amount of extracellular substrates synthesized was recovered.

TABLE 4

| Compound | IL-1 inhibitory activity (%) | |
|---|---|---|
| (Example No.) | 1 μM | 10 μM |
| 28 | 34 | 44 |
| 36 | 22 | 48 |
| 41 | 17 | 50 |
| 53 | 39 | 71 |
| 64 | 23 | 50 |

Test Example 5

Antigen-Responsive T Cell Growth Inhibitory Activity

According to the method of Test Example 1, adjuvant arthritis was induced in Lewis rats (male, 7 weeks old). After 14 days, lymphonodi inguinales were excised. Then, a single-cell suspension was prepared by using RPMI-1640 medium containing 5% fetal bovine serum and then incubated at 37° C. for 1 hour in a nylon wool column. The cells were eluted from the column with the same medium. The non-adsorptive cell-fraction was used as T cells.

On the other hand, spleen cells were taken out from unsensitized Lewis rats (male, 8 to 9 weeks old) and irradiated with soft X-rays (20,000 R). To the spleen cells ($1\times10^5$ cells/well) were added the above T cells ($5\times10^5$ cells/well), PPD (Purified Protein Derivatives; final concentration: 2 μg/ml) and 2% Lewis rat serum (treated at 56° C. for 30 minutes). The mixture was incubated at 37° C. for 72 hours in a 5% carbonic acid incubator. Further, $^3$H-Tdr (0.5 μCi/well) was added followed by incubation for 24 hours. The cells were recovered, and the radioactivity of $^3$H-Tdr incorporated into the cells was determined. The test drug was added to the cell suspension just before the addition of PPD, and effects on incorporation of $^3$H-Tdr into the cells were observed.

The results are shown in Table 5. The compound of the present invention has inhibitory activity against stimulation of T cell growth by PPD.

TABLE 5

| Compound | Antigen-responsive T cell growth inhibitory rate (%) | |
|---|---|---|
| (Example No.) | 1 μM | 10 μM |
| 36 | 33 | 79 |
| 45 | 36 | 70 |
| 46 | 39 | 92 |
| 47 | 61 | 93 |
| 53 | 51 | 91 |
| 60 | 59 | 91 |
| 64 | 53 | 78 |

The following Reference Examples (RE) and Examples (Ex) further illustrate the present invention in detail, but are no to be construed to limit the scope thereof.

REFERENCE EXAMPLE 1

Conc. sulfuric acid (0.3 ml) was added to a mixture of 2-amino-3',4'-dimethoxy-4,5-ethylenedioxybenzophenone (6.5 g), ethyl 4-chloroacetoacetate (3.7 g) and acetic acid (60 ml), and the resulting mixture was stirred at 100° C. for 3 hours. The reaction mixture was concentrated under reduced pressure, and the residue was poured into water. The mixture was made alkaline with 2N NaOH and extracted with chloroform. The chloroform layer was washed with water and dried ($MgSO_4$), and the solvent was distilled off under reduced pressure. The residue was subjected to column chromatography on silica gel. From the fraction eluted with chloroform/ethyl acetate (7:3, v/v), ethyl 2-chloromethyl-4-(3,4-dimethoxyphenyl)-6,7-ethylenedioxyquinoline-3-carboxylate (5.5 g, 60%) was obtained and recrystallized from acetone.

Colorless prisms. mp. 197–198° C. Elemental Analysis: Calcd. for $C_{23}H_{22}NO_6Cl$: C,62.24; H,5.00; N,3.16 Found: C,61.95; H,5.15; N,3.01.

REFERENCE EXAMPLES 2 to 25

According to the same manner as that described in Reference Example 1, compounds in Tables 6 to 8 were obtained.

TABLE 6
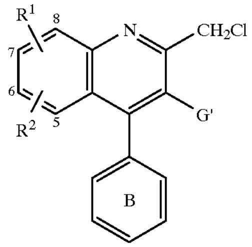
| RE No | $R^1$, $R^2$ | 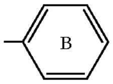 | G' | yield (%) | mp (°C.) | recrystallization solvent |
|---|---|---|---|---|---|---|
| 2 | 6-Cl, H | 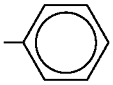 | $COOC^2H_5$ | 61 | 105–106 | ethanol/water |
| 3 | 6-Cl, H | 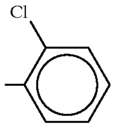 | $COOC_2H_5$ | 27 | 112–114 | methanol/water |
| 4 | 6-Cl, H | 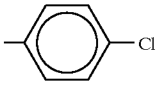 | $COOC_2H_5$ | 42 | 140–141 | ethyl acetate/hexane |
| 5 | 6-Cl, H | 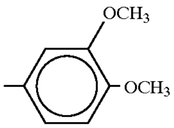 | $COOC_2H_5$ | 44 | 135–136 | ethyl acetate/ether |
| 6 | 6-$CH_3$, H | 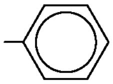 | $COOC_2H_5$ | 42 | 78–79 | ethyl acetate/hexane |
| 7 | 7-$CH_3$, H | 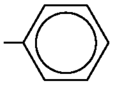 | $COOC_2H_5$ | 40 | 125–126 | acetone/ether |
| 8 | 6-Br, H | 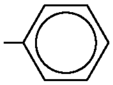 | $COOC_2H_5$ | 58 | 108–109 | acetone/isopropyl ether |
| 9 | 6-$CF_3$, H | 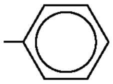 | $COOC_2H_5$ | 80 | note 1) oil | — |
| 10 | 6, 7-$(CH_3)_2$ | 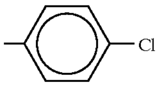 | $COOC_2H_5$ | 70 | 170–171 | ethyl acetate |

TABLE 6-continued
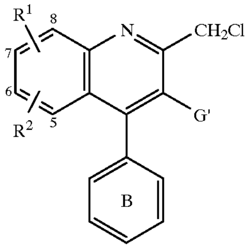
| RE No | $R^1$, $R^2$ | 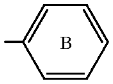 | G' | yield (%) | mp (°C.) | recrystallization solvent |
|---|---|---|---|---|---|---|
| 11 | 6, 7-$(CH^3)_2$ | 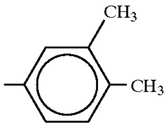 | $COOC_2H_5$ | 42 | 119–120 | ethyl acetate/hexane |
Note 1)
NMR (δppm) in $CDCl_3$: 0.92(3H, t, J=7.2Hz), 4.06(2H, q, J=7.2Hz), 5.03(2H, s), 7.33–7.37(2H, m), 7.50–7.55(3H, m), 7.90–7.98(2H, m), 8.26(1H, d, J=9.4Hz).
TABLE 7
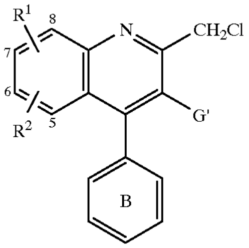
| RE No | $R^1$, $R^2$ | 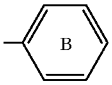 | G' | Yield (%) | mp (°C.) | recrystallization solvent |
|---|---|---|---|---|---|---|
| 12 | 6, 7-$(OCH^2CH_2O)$ | 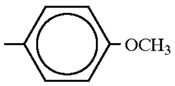 | $COOC_2H_5$ | 44 | 155–156 | acetone/ether |
| 13 | 6, 7-$(CH_3O)_2$ | 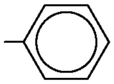 | $COOC_2H_5$ | 23 | 153–155 | acetone/ether |
| 14 | 6, 7-$(CH_3O)_2$ | 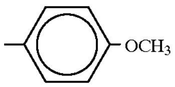 | $COOC_2H_5$ | 48 | 108–109 | ether |

TABLE 7-continued
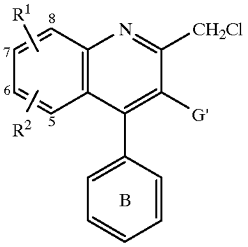
| RE No | $R^1$, $R^2$ | 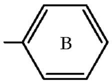 | G' | Yield (%) | mp (°C.) | recrystallization solvent |
|---|---|---|---|---|---|---|
| 15 | 6, 7-$(CH^3O)_2$ | 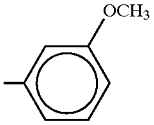 | $COOC_2H_5$ | 81 | 75–76 | isopropyl ether |
| 16 | 6, 7-$(CH_3O)_2$ | 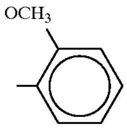 | $COOC_2H_5$ | 53 | 146–147 | ethyl acetate/hexane |
| 17 | 6, 7-$(CH_3O)_2$ | 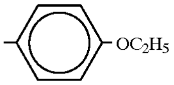 | $COOC_2H_5$ | 50 | 151–153 | ethyl acetate/hexane |
| 18 | 6, 7-$(CH_3O)_2$ | 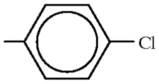 | $COOC_2H_5$ | 53 | 160–161 | ethyl acetate/hexane |
| 19 | 6, 7-$(CH_3O)_2$ | 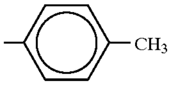 | $COOC_2H_5$ | 35 | 126–127 | acetone/ether |
| 20 | 6, 7-$(CH_3O)_2$ | 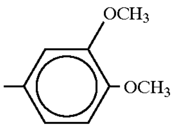 | $COOCH_3$ | 44 | 181–182 | acetone/ether |
| 21 | 6, 7-$(CH_3O)_2$ | 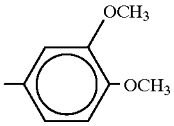 | $COOC_2H_5$ | 53 | 147–148 | acetone/ether |

TABLE 7-continued
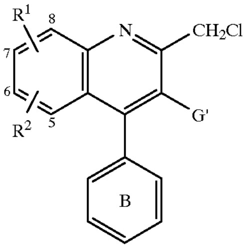
| RE No | $R^1$, $R^2$ | 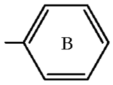 | G' | Yield (%) | mp (°C.) | recrystallization solvent |
|---|---|---|---|---|---|---|
| 22 | 6, 7-$(CH^3O)_2$ | 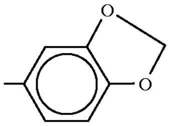 | $COOC_2H_5$ | 44 | 134–135 | ethyl acetate/hexane |
TABLE 8
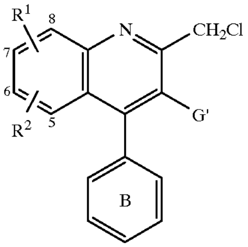
| RE No | $R^1$, $R^2$ | 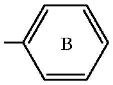 | G' | Yield (%) | mp (°C.) | recrystallization solvent |
|---|---|---|---|---|---|---|
| 23 | 6, 7-$(CH^3O)_2$ | 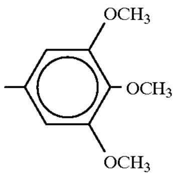 | $COOC_2H_5$ | 64 | 211–212 | chloroform/acetone |
| 24 | 6, 7-$(C_2H_5O)_2$ | 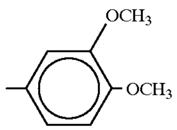 | $COOC_2H_5$ | 68 | 124–125 | ethyl acetate/hexane |
| 25 | H, H | 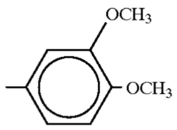 | $COOC_2H_5$ | 50 | 82–83 | ethyl acetate/hexane |

REFERENCE EXAMPLE 26

Conc. sulfuric acid was added to a mixture of 2-amino-4,5,3',4'-tetramethoxybenzophenone, ethyl acetoacetate and acetic acid. The resulting mixture was treated according to the same manner as that described in Reference Example 1 to obtain ethyl 6,7-dimethoxy-4-(3,4-dimethoxyphenyl)-2-methylquinoline-3-carboxylate (83%) which was recrystallized from ethanol.

Colorless prisms. mp. 147–148° C.

REFERENCE EXAMPLE 27

Conc. sulfuric acid was added to a mixture of 2-amino-4,5,3',4'-tetramethoxybenzophenone, propyl acetoacetate and acetic acid. The resulting mixture was treated according to the same manner as that described in Reference example 1 to obtain propyl 6,7-dimethoxy-4-(3,4- dimethoxyphenyl)-2-methylquinoline-3-carboxylate (79%) which was recrystallized from ethyl acetate/isopropyl ether.

Colorless prisms. mp. 153–155° C.

REFERENCE EXAMPLE 28

Conc. sulfuric acid was added to a mixture of 2-amino-4,5,3',4'-tetramethoxybenzophenone, butyl acetoacetate and acetic acid. The resulting mixture was treated according to the same manner as that described in Reference Example 1 to obtain butyl 6,7-dimethoxy-4-(3,4-dimethoxy- phenyl)-2-methylquinoline-3-carboxylate (53%) which was recrystallized from ethyl acetate/hexane.

Colorless prisms. mp. 119–120° C.

REFERENCE EXAMPLE 29

A mixture of ethyl 6,7-dimethoxy-4-(3,4-dimethoxyphenyl)-2-methylquinoline-3-carboxylate (411 mg), N-bromosuccinimide (NBS) (214 mg), 2,2'-azobis (isobutyronitrile) (10 mg) and carbon tetrachloride (10 ml) was stirred under reflux for 5 hours. The reaction mixture was washed with water and dried ($MgSO_4$), and the solvent was distilled off under reduced pressure. The residue was subjected to column chromatography on silica gel. From the fraction eluted with chloroform/ethyl acetate (10:1, v/v), ethyl 2-bromomethyl-6,7-dimethoxy-4-(3,4-dimethoxyphenyl)quinoline-3-carboxylate (285 mg, 58%) was obtained and recrystallized from ethyl acetate/hexane.

Colorless prisms. mp. 135–136° C. Elemental Analysis: Calcd. for $C_{23}H_{24}NO_6Br$: C,56.34; H,4.93; N,2.86 Found: C,55.98; H,5.23; N,2.62.

REFERENCE EXAMPLE 30

According to the same manner as that described in Reference Example 29, propyl 2-bromomethyl-6,7-dimethoxy-4-(3,4-dimethoxyphenyl)quinoline-3-carboxylate (48%) was obtained. This product was recrystallized from ethyl acetate/isopropyl ether.

Colorless prisms. mp. 160–161° C. Elemental Analysis: Calcd. for $C_{24}H_{26}$NO6Br: C,57.15; H,5.20; N,2.78 Found: C,56.75; H,5.30; N,2.68.

REFERENCE EXAMPLE 31

According to the same manner as that described in Reference Example 29, butyl 2-bromomethyl-6,7-dimethoxy-4- (3,4-dimethoxyphenyl)quinoline-3-carboxylate (56%) was obtained. This product was recrystallized from ethyl acetate/ether.

Colorless prisms. mp. 160–161° C. Elemental Analysis: Calcd. for $C_{25}H_{28}NO_6Br$: C,57.92; H,5.44; N,2.70 Found: C,57.96; H,5.53; N,2.50.

REFERENCE EXAMPLE 32

A mixture of ethyl 2-chloromethyl-6,7-dimethoxy-4-(3,4-dimethoxyphenyl)quinoline-3-carboxylate (3.0 g), m-chloroperoxybenzoic acid (85%, 2.3 g) and methanol (40 ml) was stirred under reflux for 2 hours. The solvent of the reaction mixture was distilled off under reduced pressure. The residue was poured into chloroform. The chloroform layer was washed with water and dried ($MgSO_4$), and then the solvent was distilled off under reduced pressure. The residue was subjected to column chromatography on silica gel. From the fraction eluted with chloroform/ethyl acetate (6:4, v/v), ethyl 2-chloromethyl-6,7-dimethoxy-4-(3,4-dimethoxyphenyl)quinoline-3-carboxylate 1-oxide (2.0 g, 65%) was obtained and recrystallized from acetone/isopropyl ether.

Colorless prisms. mp. 193–194° C. Elemental Analysis: Calcd. for $C_{23}H_{24}NO_7Cl$: C,59.81; H,5.24; N,3.03 Found: C,59.69; H,5.32; N,3.05.

REFERENCE EXAMPLE 33

Aluminum chloride powder (6.7 g) was added to a mixture of 2-amino-4,5,3',4'-tetramethoxybenzophenone (8.0 g) and chloroacetonitrile (25 ml), and the resulting mixture was stirred at 100° C. for 2 hours. The reaction mixture was poured into water and extracted with chloroform. The chloroform layer was washed with water and dried ($MgSO_4$), and the solvent was distilled off under reduced pressure. The residue was subjected to column chromatography on silica gel. From the fraction eluted with chloroform/ethyl acetate (10:1, v/v), 2-chloromethyl-6,7-dimethoxy-4-(3,4-dimethoxyphenyl)quinazoline (4.9 g., 52%) was obtained and recrystallized from acetone. Colorless prisms. mp. 183–184° C.

REFERENCE EXAMPLE 34

A mixture of ethyl 2-chloromethyl-6,7-diethoxy-4- (3,4-dimethoxyphenyl)quinoline-3-carboxylate (7.1 g), triphenylphosphine (3.9 g) and toluene (70 ml) was stirred under reflux for 2 hours. After cooling, the deposited solid was separated by filtration to obtain [6,7-diethoxy-4- (3,4-dimethoxyphenyl)-3-ethoxycarbonylquinolin-2-yl] methyltriphenylphosphonium chloride (9.6 g, 87%). mp. 172–174° C. (dec.).

REFERENCE EXAMPLE 35

According to the same manner as that described in Reference Example 34, [6,7-dimethoxy-4-(3,4-dimethoxyphenyl)-3-ethoxycarbonylquinolin-2-yl] methyltriphenylphosphonium chloride. mp. 200–202° C. (dec.).

REFERENCE EXAMPLE 36

According to the same manner as that described in Reference Example 34, [6,7-dimethoxy-4-(4-methoxyphenyl)-3- ethoxycarbonylquinolin-2-yl] methyltriphenylphosphonium chloride. mp. 178°–180° C. (dec.).

REFERENCE EXAMPLE 37

According to the same manner as that described in Reference Example 34, [6,7-dimethoxy-4-(3,4-dimethoxyphenyl)quinazolin-2-yl]methyltriphenylphosphonium chloride. mp. 208–210° C. (dec.).

REFERENCE EXAMPLE 38

According to the same manner as that described in Reference Example 1, ethyl 2-chloromethyl-4-(3,4- dimethoxyphenyl)-6-methylquinoline-3-carboxylate was obtained. This product was recrystallized from ethanol. Colorless prisms. mp. 125–126° C.

REFERENCE EXAMPLE 39

A mixture of sodium iodide (1.68 g) and methyl ethyl ketone (15 ml) was stirred at 80° C. for 1 hour. Then ethyl 2-chloro-6,7-dimethoxy-4-(3,4-dimethoxyphenyl) quinoline-3-carboxylate (2.0 g) was added, and the resulting mixture was stirred at the same temperature for 12 hours. The insoluble materials were filtered off, and the filtrate was concentrated under reduced pressure. The residue was poured into water and extracted with ethyl acetate. The ethyl acetate layer was washed with water and dried ($MgSO_4$), and the solvent was distilled off. The residual oil was subjected to column chromatography on silica gel. From the fraction eluted with chloroform/ethyl acetate (1:1, v/v), ethyl 6,7-dimethoxy-4-(3,4-dimethoxyphenyl)-2-iodomethylquinoline-3-carboxylate (1.4 9, 58%) was obtained and recrystallized from ethyl acetate/hexane.

Colorless prisms. mp. 170–171° C. Elemental Analysis: Calcd. for $C_{23}H_{24}NO_6I$: C,51.41; H,4.50; N,2.61 Found: C,51.25; H,4.53; N,2.58.

EXAMPLE 1

A mixture of ethyl 2-chloromethyl-6,7-dimethoxy-4-(3,4-dimethoxyphenyl)quinoline-3-carboxylate (3.0 g), 1-ethyl-2-mercaptoimidazole (1.0 g), potassium carbonate (1.1 g) and N,N-dimethylformamide (30 ml) was stirred at room temperature for 3 hours. The reaction mixture was poured into water and extracted with ethyl acetate. The ethyl acetate layer was washed with water and dried ($MgSO_4$), and the solvent was distilled off under reduced pressure. The residue was subjected to column chromatography on silica gel. From the fraction eluted with chloroform/ethyl acetate (3:2, v/v), ethyl 2-[(1-ethylimidazol-2-yl)thiomethyl]-6,7-dimethoxy-4-(3,4-dimethoxyphenyl)quinoline-3-carboxylate (2.8 g, 78%) was obtained and recrystallized from ethyl acetate/hexane.

Colorless prisms. mp. 157–158° C. Elemental Analysis: Calcd. for $C_{28}H_{31}N_3O_6S$: C,62.55; H,5.81; N,7.82 Found: C,62.55; H,5.84; N,7.79.

EXAMPLE 2 m-Chloroperoxybenzoic acid (85%, 830 mg) was added in small portions under ice-cooling to a solution of ethyl 6,7-dimethoxy-4-(3,4-dimethoxyphenyl)-2-[(1-methylimidazol- 2-yl)thiomethyl]quinoline-3-carboxylate (3.0 g) in dichloromethane (75 ml). The reaction mixture was stirred at room temperature for 2.5 hours, washed successively with 5% $NaHSO_3$ aqueous solution, saturated aqueous solution of sodium bicarbonate and water, and dried ($MgSO_4$). The solvent was distilled off under reduced pressure. The residue was subjected to column chromatography on silica gel. From the fraction eluted with ethyl acetate/methanol (10:1, v/v), ethyl 6,7-dimethoxy-4-(3,4-dimethoxyphenyl)-2- [(1-methylimidazol-2-yl) sulfinylmethyl]quinoline-3-carboxylate (1.8 g, 58%) was obtained and recrystallized from acetone-ethyl ether.

Colorless prisms. mp. 193–194° C. Elemental Analysis: Calcd. for $C_{27}H_{29}N_3O_7S$: C,60.10; H,5.42; N,7.79 Found: C,59.80; H,5.60; N,7.51.

EXAMPLE 3

According to the same manner as that described in Example 2, ethyl 2-[(2-benzimidazolyl)sulfinylmethyl]-6,7-dimethoxy-4-(3,4-dimethoxyphenyl)quinoline-3-carboxylate was obtained. This product was recrystallized from acetone.

Colorless prisms. mp. 160–161° C. Elemental Analysis: Calcd. for $C_{30}H_{29}N_3O_7S$: C,62.60; H,5.08; N,7.30 Found: C,62.21; H,5.10; N,7.09.

EXAMPLE 4 m-Chloroperoxybenzoic acid (85%, 2.5 9) was added in small portions under ice-cooling to a solution of ethyl 6,7-dimethoxy-4-(3,4-dimethoxyphenyl)-2-[(1-methylimidazol- 2-yl)thiomethyl]quinoline-3-carboxylate (2.5 g) in dichloromethane (60 ml). The reaction mixture was stirred at room temperature for 4 hours, washed successively with 5% $NaHSO_3$ aqueous solution, saturated aqueous solution of sodium bicarbonate and water, and dried ($MgSO_4$). The solvent was distilled off under reduced pressure. The residue was subjected to column chromatography on silica gel. From the fraction eluted with ethyl acetate/methanol (10:1, v/v), ethyl 6,7-dimethoxy-4-(3,4-dimethoxyphenyl)-2- [(1-methylimidazol-2-yl) sulfonylmethyl]quinoline-3-carboxylate (1.5 g, 58%) was obtained and recrystallized from acetone/ethyl ether.

Colorless prisms. mp. 183–184° C. Elemental Analysis: Calcd. for $C_{27}H_{29}N_3O_8S$: C,58.37; H,5.26; N,7.56 Found: C,58.46; H,5.24; N,7.20.

EXAMPLE 5

According to the same manner as that described in Example 4, ethyl 2-[(2-benzimidazolyl)sulfonylmethyl]-6,7- dimethoxy-4-(3,4-dimethoxyphenyl)quinoline-3-carboxylate was obtained. This product was recrystallized from acetone/isopropyl ether.

Colorless prisms. mp. 181–182° C. Elemental Analysis: Calcd. for $C_{30}H_{29}N_3O_8S$: C,60.90; H,4.94; N,7.10 Found: C,60.76; H,4.86; N,7.09.

EXAMPLE 6

A solution of hydrogen chloride in ethanol (27%, 1.3 g) was added dropwise at room temperature to a solution of ethyl 6,7-dimethoxy-4-(3,4-dimethoxyphenyl)-2-[(1-methylimidazol-2-yl)thiomethyl]quinoline-3-carboxylate (4.9 g) in ethanol (100 ml). About two thirds of the solvent was distilled off under reduced pressure. Ethyl ether was added to the residue, and the deposited crystals were separated by filtration. The separated crystals were recrystallized from isopropanol to obtain ethyl 6,7-dimethoxy-4-(3,4-dimethoxyphenyl)-2-[(1-methylimidazol-2-yl)thiomethyl] quinoline-3-carboxylate hydrochloride monohydrate (3.0 g, 55%).

Colorless prisms. mp. 133–134° C. Elemental Analysis: Calcd. for $C_{27}H_{29}N_3O_6S.HCl.H_2O$ C,56.10; H,5.58; N,7.27 Found: C,55.84; H,5.72; N,7.16.

EXAMPLE 7

A mixture of propyl 2-bromomethyl-6,7-dimethoxy-4-(3,4-dimethoxyphenyl)quinoline-3-carboxylate (3.3 g), 2-mercapto-1-methylimidazole (821 mg), potassium carbonate (1.08 g) and N,N-dimethylformamide (60 ml) was stirred at room temperature for 3 hours. The reaction mixture was poured into water and extracted with ethyl acetate. The ethyl acetate layer was washed with water and dried ($MgSO_4$), and the solvent was distilled off under reduced pressure. The residue was subjected to column chromatography on silica gel. From the fraction eluted with chloroform/ethyl acetate (7:3, v/v), propyl 6,7-dimethoxy-4-(3,4-dimethoxyphenyl)-2- [(1-methylimidazol-2-yl) thiomethyl]quinoline-3-carboxylate (1.77 g, 51%) was obtained and recrystallized from acetone/isopropyl ether.

Colorless prisms. mp. 131–132° C. Elemental Analysis: Calcd. for $C_{28}H_{31}N_3O_6S$: C,62.55; H,5.81; N,7.82 Found: C,62.18; H,5.72; N,7.73.

EXAMPLE 8

According to the same manner as that described in Example 7, butyl 6,7-dimethoxy-4-(3,4-dimethoxyphenyl)-2- [(1-methylimidazol-2-yl)thiomethyl]quinoline-3-carboxylate was obtained (60%). This product was recrystallized from ethyl acetate/hexane.

Colorless prisms. mp. 131–132° C. Elemental Analysis: Calcd. for $C_{29}H_{33}N_3O_6S$: C,63.14; H,6.03; N,7.62 Found: C,62.87; H,6.00; N,7.39.

EXAMPLE 9

According to the same manner as that described in Example 1, methyl 6,7-dimethoxy-4-(3,4-dimethoxyphenyl)-2- [(1-methylimidazol-2-yl)thiomethyl] quinoline-3-carboxylate was obtained (69%). This product was recrystallized from acetone/ether Colorless prisms. mp. 159–160° C. Elemental Analysis: Calcd. for $C_{26}H_{27}N_3O_6S$: C,61.28; H,5.34; N,8.25 Found: C,61.05; H,5.59; N,8.13.

EXAMPLE 10

According to the same manner as that described in Example 1, ethyl 6,7-dimethoxy-4-(2-methoxyphenyl)-2-[(1- methylimidazol-2-yl)thiomethyl]quinoline-3-carboxylate was obtained (89%) as an oil.

NMR (δppm) in $CDCl_3$: 0.90 (3H,t,J=7Hz), 3.34 (3H,s), 3.70 (3H,s), 3.74 (3H,s), 3.98 (2H,q,J=7Hz), 4.03 (3H,s), 4.64 (2H,s), 6.66 (1H,s), 6.86 (1H,s), 7.01–7.16 (4H,m), 7.34 (1H,s), 7.45 (1H,doublet t,J=8 and 2Hz).

This oil was dissolved in ethanol (15 ml), and a solution (23%, 1.2 g) of hydrogen chloride in ethanol was added. The solvent was distilled off under reduced pressure to obtain ethyl 6,7-dimethoxy-4-(2-methoxyphenyl)-2-[(1-methylimidazol-2-yl)thiomethyl]quinoline-3-carboxylate hydrochloride (2.0 g) which was recrystallized from ethanol/ether.

Pale yellow prisms. mp. 180–181° C. Elemental Analysis: Calcd. for $C_{26}H_{27}N_3O_5S.HCl.1/2H_2O$ C,57.93; H,5.42; N,7.80 Found: C,58.05; H,5.32; N,7.72.

EXAMPLE 11

According to the same manner as that described in Example 1, ethyl 6,7-dimethyl-4-(3,4-dimethylphenyl)-2-[(1- methylimidazol-2-yl)thiomethyl]quinoline-3-carboxylate was obtained (97%) as an oil.

NMR (δppm) in $CDCl_3$: 0.93 (3H,t,J=7Hz), 2.31 (3H,s), 2.32 (3H,s), 2.35 (3H,s), 2.44 (3H,s), 3.42 (3H,s), 4.03 (2H,q,J=7Hz), 4.61 (2H,s), 6.88 (1H,d,J=1Hz), 7.03–7.10 (3H,m), 7.23 (1H,d,J=8Hz), 7.35 (1H,s), 7.78 (1H,s).

This oil was dissolved in ethanol (10 ml), and a solution (23%, 0.584 g) of hydrogen chloride in ethanol was added. The solvent was distilled off under reduced pressure to obtain ethyl 6,7-dimethyl-4-(3,4-dimethylphenyl)-2-[(1-methylimidazol-2-yl)thiomethyl]quinoline-3-carboxylate hydrochloride (1.1 g) which was recrystallized from ethanol/ether.

Pale yellow prisms. mp. 133–134° C. Elemental Analysis: Calcd. for $C_{27}H_{29}N_3O_2S.HCl.3/2H_2O$ C,62.00; H,6.36; N,8.03 Found: C,62.31; H,6.01; N,7.98.

EXAMPLE 12

According to the same manner as that described in Example 1, ethyl 6,7-dimethoxy-4-(3,4-dimethoxyphenyl)-2-[(1-methylimidazol-2-yl)thiomethyl]quinoline-3-carboxylate 1-oxide was obtained (69%). This product was recrystallized from ethyl acetate/hexane.

Colorless prisms. mp. 171–172° C. Elemental Analysis: Calcd. for $C_{27}H_{29}N_3O_7S$: C,60.10; H,5.42; N,7.79 Found: C,60.29; H,5.53; N,7.49.

EXAMPLES 13 TO 72

According to the same manner as that described in Example 1, the compounds in Tables 9 to 17 were obtained.

TABLE 9

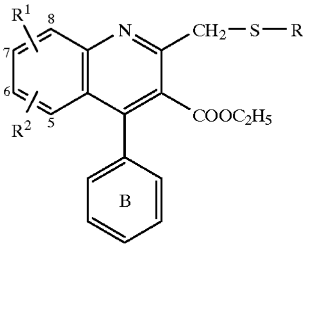

| Ex No | $R^1$, $R^2$ | 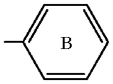 | R | Yield (%) | mp (°C.) | Recrystallization solvent |
|---|---|---|---|---|---|---|
| 13 | H, H | 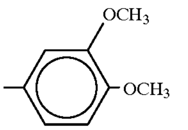 | 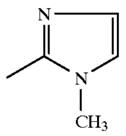 | 95 | 141–142 | ethyl acetate/hexane |

TABLE 9-continued
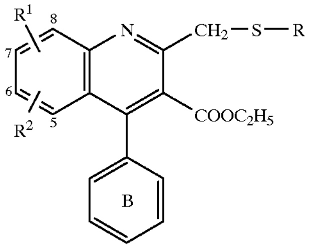
| Ex No | $R^1$, $R^2$ | 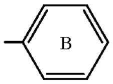 | R | Yield (%) | mp (°C.) | Recrystallization solvent |
|---|---|---|---|---|---|---|
| 14 | 6-Cl, H | 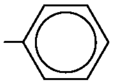 | 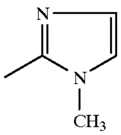 | 65 | 128–129 | ethyl acetate/hexane |
| 15 | 6-Cl, H | 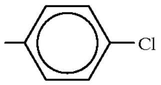 | 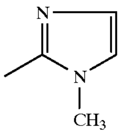 | 64 | 117–118 | ethyl acetate/hexane |
| 16 | 6-Cl, H | 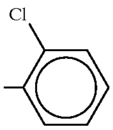 | 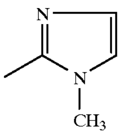 | 48 | 137–138 | acetone/ether |
| 17 | 6-Cl, H | 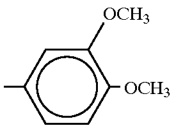 | 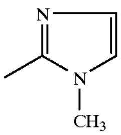 | 71 | 120–121 | acetone/isopropyl ether |
| 18 | 6-Cl, H | 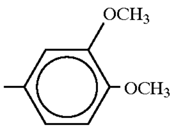 | 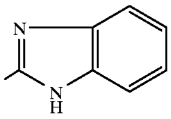 | 55 | 190–191 | acetone/isopropyl ether |
| 19 | 6-$CH^3$, H | 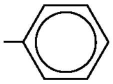 | 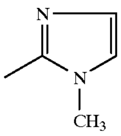 | 58 | 132–133 | ethyl acetate/hexane |

TABLE 10
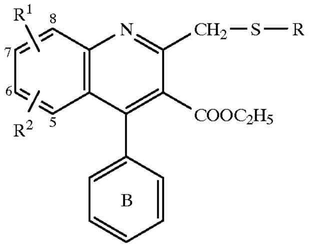
| Ex No | $R^1$, $R^2$ | 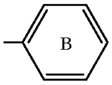 | R | Yield (%) | mp (°C.) | Recrystallization solvent |
|---|---|---|---|---|---|---|
| 20 | 7-$CH^3$, H | 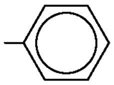 | 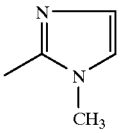 | 58 | 98–99 | ethyl acetate/hexane |
| 21 | 6-Br, H | 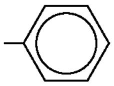 | 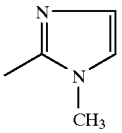 | 69 | 129–130 | ethyl acetate/hexane |
| 22 | 6-$CF_3$, H | 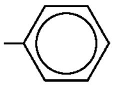 | 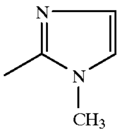 | 54 | 108–109 | ethyl acetate/hexane |
| 23 | 6, 7-$(CH_3)_2$ | 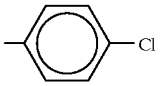 | 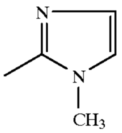 | 64 | 114–115 | ethyl acetate/hexane |
| 24 | 6, 7-$(OCH_2CH_2O)$ | 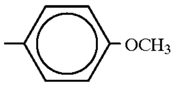 | 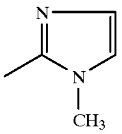 | 69 | 180–181 | acetone/ether |
| 25 | 6, 7-$(OCH_2CH_2O)$ | 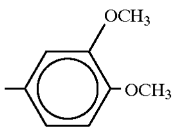 | 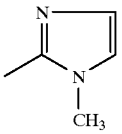 | 60 | 120–121 | acetone |
| 26 | 6, 7-$(CH_3O)_2$ | 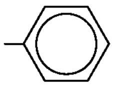 | 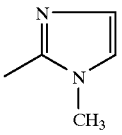 | 60 | 101–102 | acetone/ether |

TABLE 11
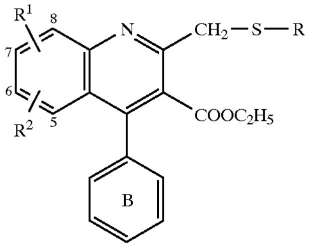
| Ex No | $R_1$, $R^2$ | 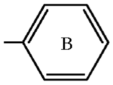 | R | Yield (%) | mp (°C.) | Recrystallization solvent |
|---|---|---|---|---|---|---|
| 27 | 6, 7-$(CH^3O)_2$ | 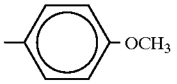 | 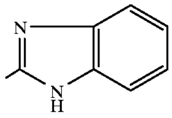 | 85 | 105–107 | ether |
| 28 | 6, 7-$(CH_3O)_2$ | 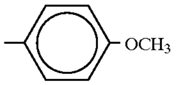 | 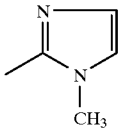 | 72 | 123–124 | ether |
| 29 | 6, 7-$(CH_3O)_2$ | 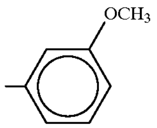 | 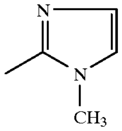 | 57 | 99–100 | ethyl acetate/hexane |
| 30 | 6, 7-$(CH_3O)_2$ | 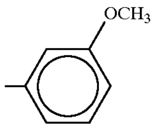 | 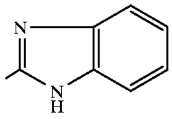 | 48 | 102–103 | isopropyl ether |
| 31 | 6, 7-$(CH_3O)_2$ | 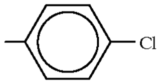 | 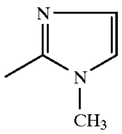 | 74 | 132–133 | ethyl acetate/hexane |
| 32 | 6, 7-$(CH_3O)_2$ | 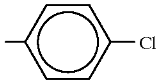 | 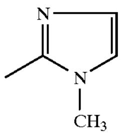 | 74 | 132–133 | ethyl acetate/hexane |
| 33 | 6, 7-$(CH_3O)_2$ | 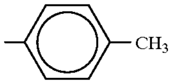 | 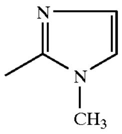 | 46 | 134–135 | acetone/ether |

TABLE 12
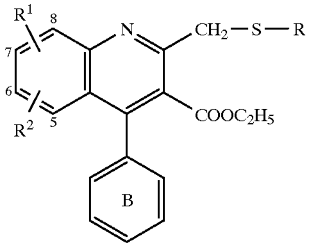
| Ex No | $R_1$, $R^2$ | 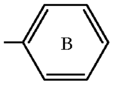 | R | Yield (%) | mp (°C.) | Recrystallization solvent |
|---|---|---|---|---|---|---|
| 34 | 6, 7-$(CH^3O)_2$ | 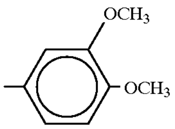 | 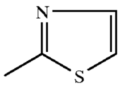 | 81 | 145–146 | ethyl acetate/hexane |
| 35 | 6, 7-$(CH_3O)_2$ | 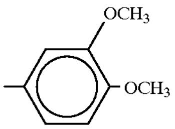 | 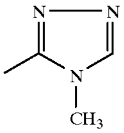 | 77 | 147–148 | acetone/isopropyl ether |
| 36 | 6, 7-$(CH_3O)_2$ | 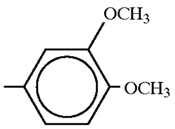 | 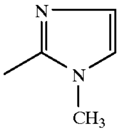 | 84 | 149–150 | acetone/ether |
| 37 | 6, 7-$(CH_3O)_2$ | 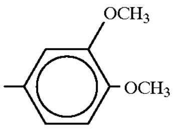 | 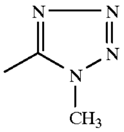 | 76 | 176–177 | acetone/ether |
| 38 | 6, 7-$(CH_3O)_2$ | 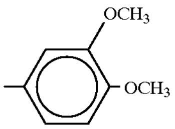 | 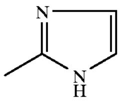 | 65 | 111–112 | acetone/ether |
| 39 | 6, 7-$(CH_3O)_2$ | 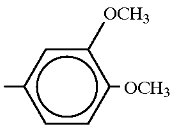 | 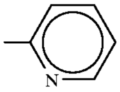 | 88 | 162–163 | acetone |
| 40 | 6, 7-$(CH_3O)_2$ | 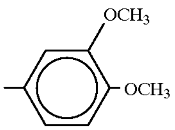 | 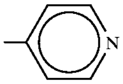 | 77 | 185–186 | acetone |

TABLE 13
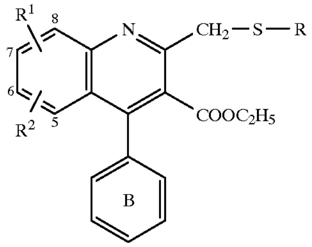
| Ex No | R1, $R^2$ | 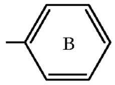 | R | Yield (%) | mp (°C.) | Recrystallization solvent |
|---|---|---|---|---|---|---|
| 41 | 6, 7-$(CH^3O)_2$ | 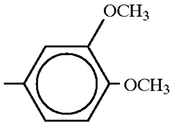 | 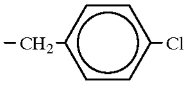 | 90 | 165–166 | ether |
| 42 | 6, 7-$(CH_3O)_2$ | 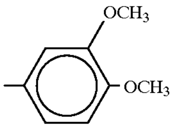 | 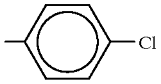 | 83 | 152–153 | ether |
| 43 | 6, 7-$(CH_3O)_2$ | 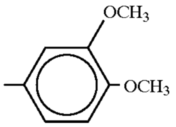 | 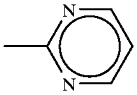 | 86 | 174–176 | ether |
| 44 | 6,. 7-$(CH_3O)_2$ | 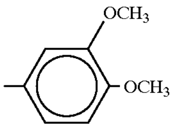 | 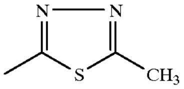 | 80 | 184–185 | acetone |
| 45 | 6, 7-$(CH_3O)_2$ | 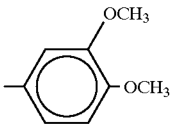 | 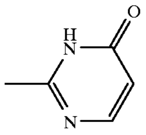 | 72 | 186–187 | ethyl acetate/hexane |
| 46 | 6, 7-$(CH_3O)_2$ | 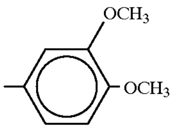 | 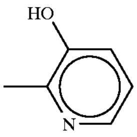 | 83 | 219–220 | ethyl acetate/hexane |
| 47 | 6, 7-$(CH_3O)_2$ | 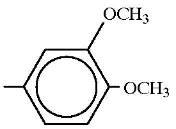 | 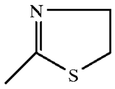 | 63 | 190–191 | ethyl acetate/hexane |

TABLE 14
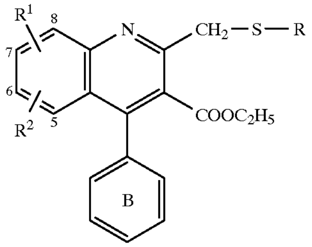
| Ex No | $R_1$, $R^2$ | 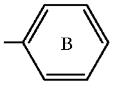 | R | Yield (%) | mp (°C.) | Recrystallization solvent |
|---|---|---|---|---|---|---|
| 48 | 6, 7-$(CH^3O)_2$ | 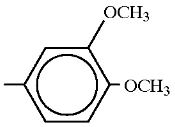 | 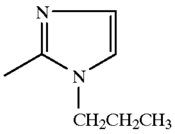 | 77 | 132–133 | ethyl acetate/hexane |
| 49 | 6, 7-$(CH_3O)_2$ | 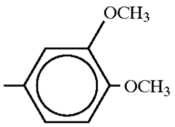 | 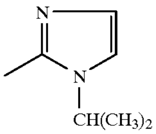 | 67 | 122–123 | ethyl acetate/hexane |
| 50 | 6, 7-$(CH_3O)_2$ | 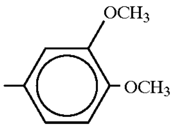 | 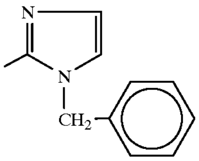 | 48 | 159–160 | ethyl acetate/hexane |
| 51 | 6, 7-$(CH_3O)_2$ | 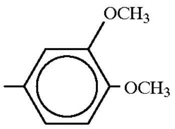 | 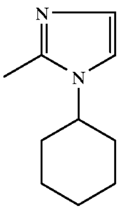 | 51 | 142–143 | ethyl acetate/hexane |
| 52 | 6, 7-$(CH_3O)_2$ | 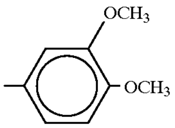 | 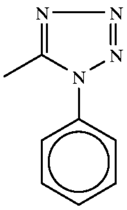 | 72 | 151–152 | ethyl acetate/ether |
| 53 | 6, 7-$(CH_3O)_2$ | 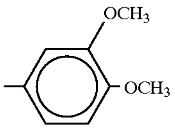 | 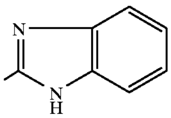 | 64 | 188–189 | acetone/isopropyl ether |

TABLE 14-continued
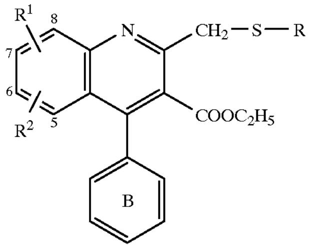
| Ex No | $R_1$, $R^2$ | 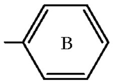 | R | Yield (%) | mp (°C.) | Recrystallization solvent |
|---|---|---|---|---|---|---|
| 54 | 6, 7-($CH^3O$)$_2$ | 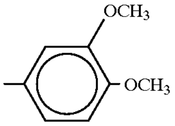 | 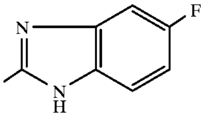 | 82 | 188–190 | acetone/isopropyl ether |
TABLE 15
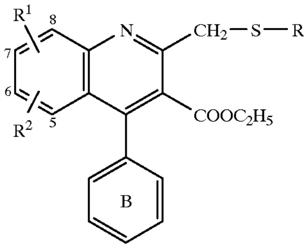
| Ex No | $R_1$, $R^2$ | 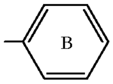 | R | Yield (%) | mp (°C.) | Recrystallization solvent |
|---|---|---|---|---|---|---|
| 55 | 6, 7-($CH^3O$)$_2$ | 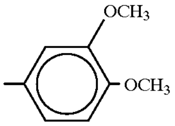 | 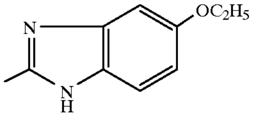 | 85 | 155–156 | methanol |
| 56 | 6, 7-($CH_3O$)$_2$ | 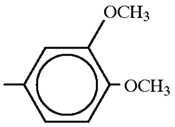 | 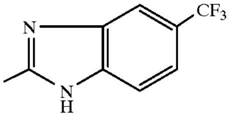 | 77 | 173–174 | ether/isopropyl ether |
| 57 | 6, 7-($CH_3O$)$_2$ | 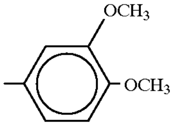 | 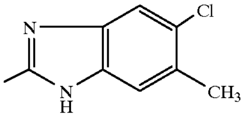 | 92 | 212–213 | ether/isopropyl ether |

TABLE 15-continued
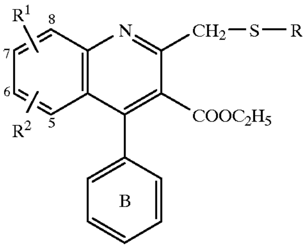
| Ex No | $R_1$, $R^2$ | 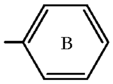 | R | Yield (%) | mp (°C.) | Recrystallization solvent |
|---|---|---|---|---|---|---|
| 58 | 6, 7-$(CH^3O)_2$ | 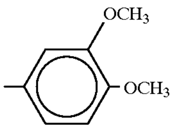 | 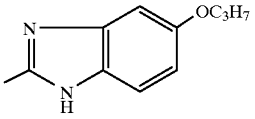 | 72 | 118–120 | ether/hexane |
| 59 | 6, 7-$(CH_3O)_2$ | 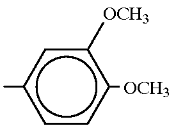 | 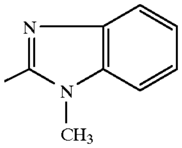 | 71 | 182–183 | acetone/isopropyl ether |
| 60 | 6, 7-$(CH_3O)_2$ | 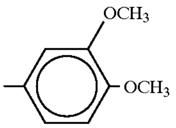 | 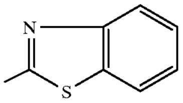 | 88 | 160–161 | ethyl acetate/hexane |
| 61 | 6, 7-$(CH_3O)_2$ | 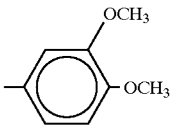 | 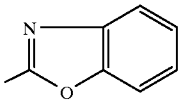 | 80 | 169–170 | ether |

TABLE 16
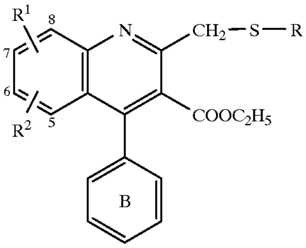
| Ex No | $R_1$, $R^2$ | 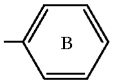 | R | Yield (%) | mp (°C.) | Recrystallization solvent |
|---|---|---|---|---|---|---|
| 62 | 6, 7-$(CH^3O)_2$ | 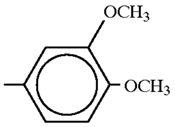 | 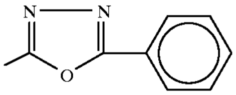 | 42 | 151–152 | acetone/ether |
| 63 | 6, 7-$(CH_3O)_2$ | 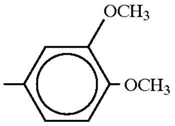 | 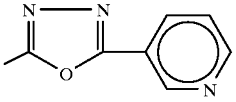 | 36 | 167–168 | acetone/ether |
| 64 | 6, 7-$(CH_3O)_2$ | 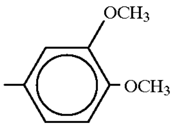 | 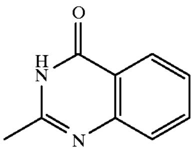 | 81 | 183–184 | ethyl acetate |
| 65 | 6, 7-$(CH_3O)_2$ | 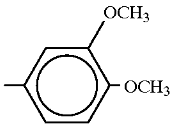 | 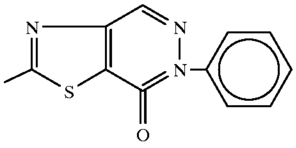 | 71 | 235–237 | dichloromethane/ether |
| 66 | 6, 7-$(CH_3O)_2$ | 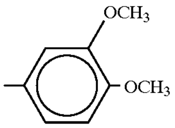 | 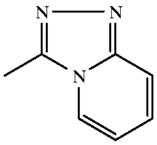 | 89 | 198–199 | methanol |
| 67 | 6, 7-$(CH_3O)_2$ | 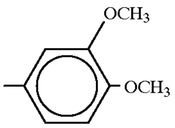 | 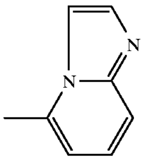 | 83 | 170–171 | acetone |

TABLE 16-continued
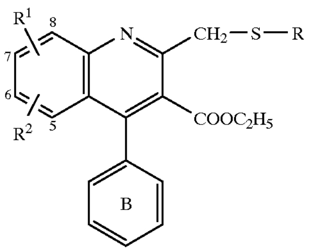
| Ex No | $R_1$, $R^2$ | 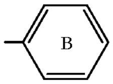 | R | Yield (%) | mp (°C.) | Recrystallization solvent |
|---|---|---|---|---|---|---|
| 68 | 6, 7-$(CH^3O)_2$ | 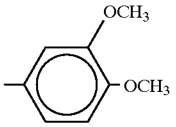 | 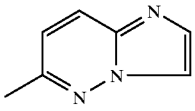 | 88 | 110–112 | methanol |
TABLE 17
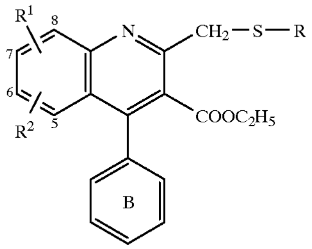
| Ex No | $R_1$, $R^2$ | 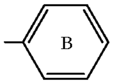 | R | Yield (%) | mp (°C.) | Recrystallization solvent |
|---|---|---|---|---|---|---|
| 69 | 6, 7-$(CH^3O)_2$ | 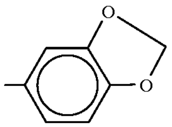 | 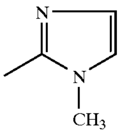 | 70 | 176–177 | ethyl acetate/hexane |
| 70 | 6, 7-$(CH_3O)_2$ | 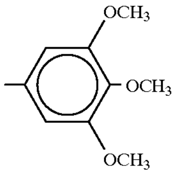 | 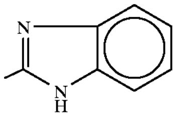 | 85 | 152–153 | acetone/isopropyl ether |

TABLE 17-continued
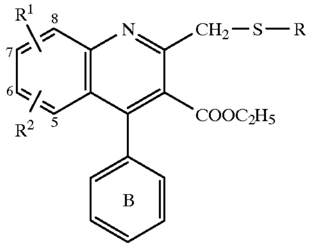
| Ex No | $R_1$, $R^2$ | 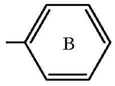 | R | Yield (%) | mp (°C.) | Recrystallization solvent |
|---|---|---|---|---|---|---|
| 71 | 6, 7-$(CH^3O)_2$ | 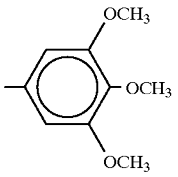 | 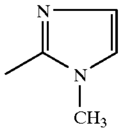 | 86 | 131–132 | acetone/isopropyl ether |
| 72 | 6, 7-$(C_2H_5O)_2$ | 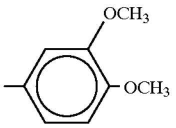 | 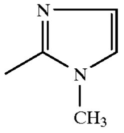 | 73 | 132–133 | ethyl acetate/hexane |
EXAMPLES 73 TO 75
According to the same manner as that described in Example 1, the compounds in Table 18 were obtained.
TABLE 18
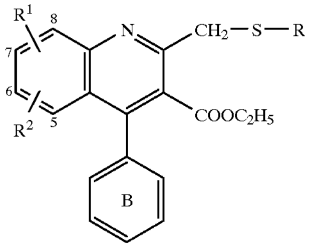
| Ex No | $R_1$, $R^2$ | 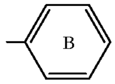 | R | Yield (%) | mp (°C.) | Recrystallization solvent |
|---|---|---|---|---|---|---|
| 73 | 6, 7-$(CH^3O)_2$ | 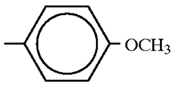 | 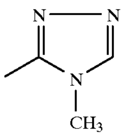 | 79 | 145–146 | ethyl acetate/hexane |

TABLE 18-continued

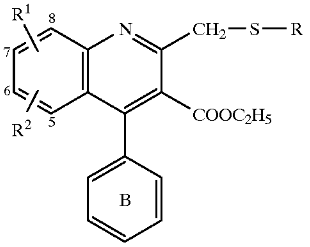

| Ex No | $R^1$, $R^2$ | 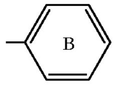 | R | Yield (%) | mp (°C.) | Recrystallization solvent |
|---|---|---|---|---|---|---|
| 74 | 6, 7-$(CH^3O)_2$ | 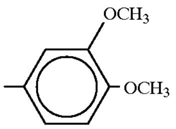 | 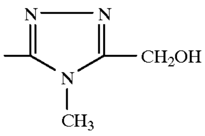 | 50 | 199–200 | dichloromethane/ethyl ether |
| 75 | 6, 7-$(CH_3O)_2$ | 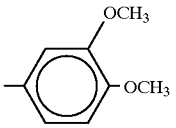 | 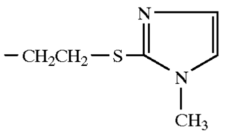 | 76 | 151–152 | ethyl acetate/hexane |

EXAMPLE 76

A mixture of 2-chloromethyl-6,7-dimethoxy-4-(3,4-dimethoxyphenyl)quinazoline (4.5 9), 2-mercaptoethanol (1.13 g), potassium carbonate (2.8 9) and N,N-dimethylformamide (50 ml) was stirred at room temperature for 2 hours. The reaction mixture was poured into water and extracted with ethyl acetate. The ethyl acetate layer was washed with water and dried ($MgSO_4$). The solvent was distilled off to obtain 6,7-dimethoxy-4-(3,4-dimethoxyphenyl)-2-[(2-hydroxyethylthio)methyl] quinazoline (4.1 g, 82%), and it was recrystallized from ethanol.

Colorless prisms. mp. 154–155° C.

EXAMPLES 77 TO 83

According to the same manner as that described in Example 76, the compounds in Table 19 were obtained.

TABLE 19
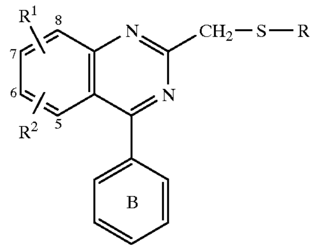
| Ex No | $R_1$, $R^2$ | 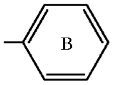 | R | Yield (%) | mp (°C.) | Recrystallization solvent |
|---|---|---|---|---|---|---|
| 77 | 6, 7-$(CH^3O)_2$ | 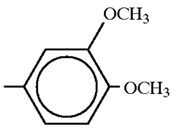 | 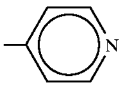 | 77 | 143–144 | acetone |
| 78 | 6, 7-$(CH_3O)_2$ | 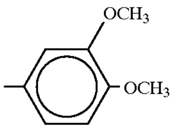 | $-CH_2COOCH_3$ | 83 | 138–139 | acetone |
| 79 | 6, 7-$(CH_3O)_2$ | 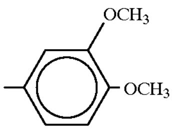 | 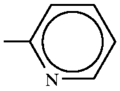 | 82 | 143–144 | acetone |
| 80 | 6, 7-$(CH_3O)_2$ | 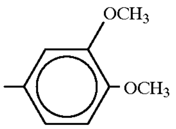 | 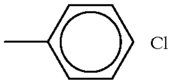 | 68 | 143–144 | acetone |
| 81 | 6, 7-$(CH_3O)_2$ | 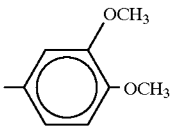 | 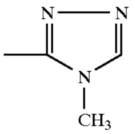 | 81 | 184–185 | acetone |
| 82 | 6, 7-$(CH_3O)_2$ | 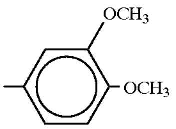 | 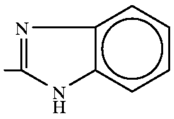 | 80 | 195–196 | acetone/isopropyl ether |
| 83 | 6, 7-$(CH_3O)_2$ | 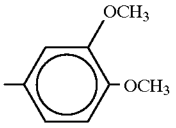 | 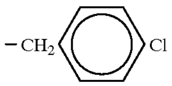 | 75 | 132–133 | ethyl ether |

EXAMPLES 84 TO 86

According to the same manner as that described in Example 2, the compounds in Table 20 were obtained.

TABLE 20

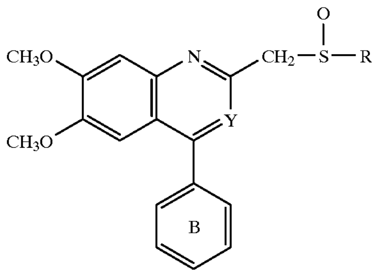

| Ex No | 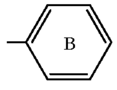 | Y | R | Yield (%) | mp (°C.) | Recrystallization solvent |
|---|---|---|---|---|---|---|
| 84 | 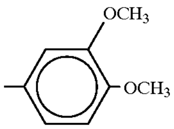 | N | 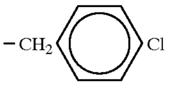 | 83 | 126–127 | acetone/isopropyl ether |
| 85 | 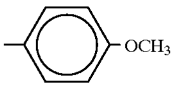 | C—$COOC_2H_5$ | 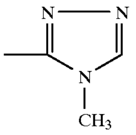 | 58 | 152–153 | ethyl acetate/hexane |
| 86 | 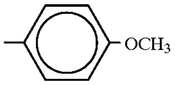 | C—$COOC_2H_5$ | 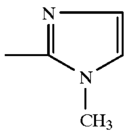 | 59 | 168–169 | ethyl acetate/hexane |

EXAMPLE 87

[6,7-Dimethoxy-4-(3,4-dimethoxyphenyl)-3-ethoxycarbonylquinolin-2-yl]methyltriphenylphosphonium chloride (17.4 g) was added at room temperature to a solution of sodium ethoxide in ethanol (prepared from Na (0.62 g) and ethanol (150 ml)). Then a solution of 2-formyl-1-methylimidazole (3.7 g) in ethanol (20 ml) was added dropwise. The mixture was stirred at room temperature for 3 hours, poured into water and extracted with ethyl acetate. The ethyl acetate layer was washed with water and dried ($MgSO_4$), and the solvent was distilled off. The residue was subjected to column chromatography on silica gel. From the fraction eluted with chloroform/methanol (100:1, v/v), ethyl (E)-6,7-dimethoxy-4-(3,4-dimethoxyphenyl)-2-[2-(1-methylimidazol-2-yl)vinyl]quinoline-3-carboxylate was obtained (8.3 g, 67%). It was recrystallized from ethyl acetate.

Colorless prisms. mp. 206–208° C.

From the fraction eluted thereafter, ethyl (Z)-6,7-dimethoxy-4-(3,4-dimethoxyphenyl)-2-[2-(1-methylimidazol-2-yl)vinyl]quinoline-3-carboxylate (2.6 9, 21%) was obtained as an oil.

NMR (δppm in $CDCl_3$): 0.96 (3H,t,J=7Hz), 3.35 (3H,s), 3.78 (3H,s), 3.87 (3H,s), 3.96 (3H,s), 3.97 (3H,s), 3.98 (2H,q,J=7Hz), 6.69 (1H,d,J=12Hz), 6.8–7.1 (7H,m), 7.13 (1H,s).

Ethyl (E)- and (Z)-6,7-dimethoxy-4-(3,4-dimethoxyphenyl)-2-[2-(1-methylimidazol-2-yl)vinyl]quinoline-3-carboxylates each were subjected to hydrogenation under an atmosphere of hydrogen at 1 atm in ethanol/tetrahydrofuran (1:1, v/v) in the presence of 5% palladium-carbon to obtain ethyl 6,7-dimethoxy-4-(3,4-dimethoxyphenyl)-2-[2-(1-methylimidazol-2-yl)ethyl]quinoline-3-carboxylate. It was recrystallized from ethanol.

Colorless prisms. mp. 147–148° C.

EXAMPLE 88

[6,7-Dimethoxy-4-(3,4-dimethoxyphenyl)quinazolin-2-yl]methyltriphenylphosphonium chloride (9.1 g) was added at room temperature to a solution of sodium ethoxide in ethanol (prepared from Na (0.394 g) and ethanol (100 ml)). Then a solution of 2-formyl-l-methylimidazole (1.7 g) in ethanol (10 ml) was added dropwise. The mixture was stirred at room temperature for 3 hours, poured into water and extracted with chloroform. The chloroform layer was washed with water and dried ($MgSO_4$), and the solvent was distilled off. The residue was subjected to column chromatography on silica gel. From the fraction eluted with chloroform/methanol (20:1, v/v), (E)-6,7-dimethoxy-4-(3,4-dimethoxy- phenyl)-2-[2-(1-methylimidazol-2-yl)vinyl] quinazoline (5.1 g, 82%) was obtained and recrystallized from ethanol/chloroform.

Colorless prisms. mp. 254–255° C. Elemental Analysis: Calcd. for $C_{24}H_{24}N_4O_4.3/2H_2O$: C,62.73; H,5.92; N,12.19 Found: C,62.62; H,5.85; N,11.90.

From the fraction eluted thereafter, (Z)-6,7-dimethoxy-4-(3,4-dimethoxyphenyl)-2-[2-(1-methylimidazol-2-yl)vinyl] quinazoline (0.61 g, 10%) was obtained and recrystallized from ethanol/chloroform.

Colorless plates. mp. 180–181° C. Elemental Analysis: Calcd. for $C_{24}H_{24}N_4O_4.1/2H_2O$: C,65.29; H,5.71; N,12.69 Found: C,65.28; H,5.66; N,12.42.

(E)- and (Z)-6,7-dimethoxy-4-(3,4-dimethoxy-phenyl)-2-[2-(1-methylimidazol-2-yl)vinyl]quinazolines each were subjected to hydrogenation under an atmosphere of hydrogen at 1 atm in chloroform/acetate (1:1, v/v) in the presence of 5% palladium-carbon to obtain 6,7-dimethoxy-4-(3,4-dimethoxyphenyl)-2-[2-(1-methylimidazol-2-yl)ethyl] quinazoline. It was recrystallized from ethyl acetate.

Colorless prisms. mp. 170–171° C.

EXAMPLES 89 TO 94

According to the same manner as that described in Example 87, the compounds in Table 21 were obtained.

TABLE 21

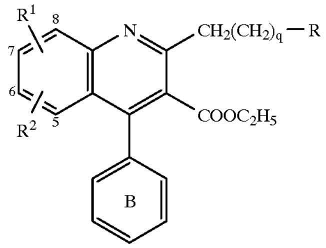

| Ex No | $R^1$, $R^2$ | 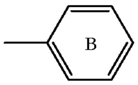 | R | q | mp (°C.) | Recrystallization solvent |
|---|---|---|---|---|---|---|
| 89 | $6,7-(CH^3O)_2$ | 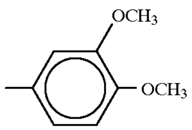 | 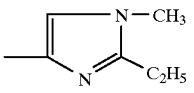 | 1 | 183–184 | ethyl acetate |
| 90 | $6,7-(CH_3O)_2$ | 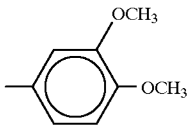 | 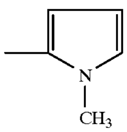 | 1 | 155–156 | ethyl acetate/ hexane |
| 91 | $6,7-(C_2H_5O)_2$ | 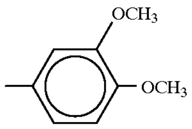 | 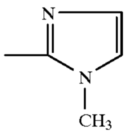 | 1 | 134–135 | ethyl acetate/ hexane |
| 92 | $6,7-(CH_3O)_2$ | 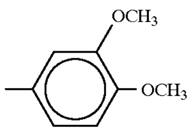 | 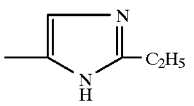 | 1 | note 1) 112–113 | ethyl acetate/ hexane |

TABLE 21-continued

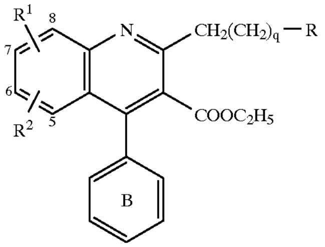

| Ex No | $R_1$, $R^2$ | 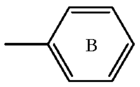 | R | q | mp (°C.) | Recrystallization solvent |
|---|---|---|---|---|---|---|
| 93 | 6,7-$(CH^3O)_2$ | 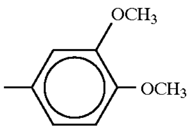 | 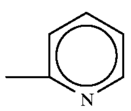 | 1 | 140–141 | ethyl acetate/ hexane |
| 94 | 6,7-$(CH_3O)_2$ | 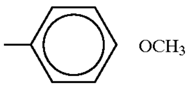 | 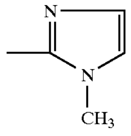 | 1 | 132–133 | ethyl acetate |

note 1) 1/2 hydrate

EXAMPLE 95

Ethyl 6,7-dimethoxy-4-(3,4-dimethoxyphenyl)-2-[2-(1-methylimidazol-2-yl)ethyl]quinoline-3-carboxylate (9.0 g) was suspended in ethanol (40 ml), and ethanolic hydrogen chloride (22%, 10 g) was added. The mixture was stirred at room temperature for 5 minutes. Ether (150 ml) was added, and the deposited crystals were separated by filtration and recrystallized from ethanol/ether to obtain ethyl 6,7-dimethoxy-4-(3,4-dimethoxyphenyl)-2-[2-(1-methylimidazol-2- yl)ethyl]quinoline-3-carboxylate dihydrochloride (9.1 g).

Pale yellow prisms. mp. 158–160° C. Elemental Analysis: Calcd. for $C_{28}H_{31}N_3O_6$.2HCl.1/3$C_2H_5$OH.1/2$H_2O$: C,57.11; H,6.02; N,6.97 Found: C,57.03; H,6.15; N,7.00.

EXAMPLE 96

[6,7-Dimethoxy-4-(3,4-dimethoxyphenyl)-3-ethoxycarbonylquinolin-2-yl]methyltriphenylphosphonium chloride (3.0 g) was added at room temperature to a solution of sodium ethoxide in ethanol (prepared from Na (0.13 g) and ethanol (45 ml)). Then a solution of 3-(1-methylimidazol-2-yl)propionaldehyde (0.787 g) was added. The mixture was stirred at room temperature for 3 hours, poured into water and extracted with ethyl acetate. The ethyl acetate layer was washed with water and dried ($MGSO_4$), and the solvent was distilled off. The residue was subjected to column chromatography on silica gel. From the fraction eluted with ethyl acetate/methanol (30:1, v/v), ethyl (E)-6,7-dimethoxy- 4-(3,4-dimethoxyphenyl)-2-[2-[2-(1-methylimidazol-2-yl)-ethyl]vinyl quinoline-3-carboxylate (0.36 g, 15%) was obtained as an oil.

NMR (δppm in $CDCl_3$): 1.03 (3H,t,J=7Hz), 2.7–3.0 (4H, m), 3.60 (3H,s), 3.79 (3H,s), 3.87 (3H,s), 3.97 (3H,s), 4.05 (3H,s), 4.09 (2H,q,J=7Hz), 6.7–7.2 (8H,m), 7.43 (1H,s).

From the fraction eluted thereafter, ethyl (Z)-6,7-dimethoxy-4-(3,4-dimethoxyphenyl)-2-[2-[2-(1-methylimidazol-2-yl)ethyl]vinyl]quinoline-3-carboxylate (0.2 g, 8%) was obtained as an oil.

NMR (δppm in $CDCl_3$): 1.02 (3H,t,J=7Hz), 2.8–3.2 (4H, m), 3.58 (3H,s), 3.80 (3H,s), 3.88 (3H,s), 3.96 (3H,s), 4.05 (3H,s), 4.07 (2H,q,J=7Hz), 6.08 (1H,dt,J=7.4&1.4Hz), 6.6–7.0 (7H,m), 7.42 (1H,s).

A mixture of ethyl (E)- and (Z)-6,7-dimethoxy-4-(3,4-dimethoxyphenyl)-2-[2-[2-(1-methylimidazol-2-yl)ethyl]-vinyl]quinoline-3-carboxylates was subjected to hydrogenation under an atmosphere of hydrogen at 1 atm in ethanol/tetrahydrofuran (1:4, v/v) in the presence of 5% palladium-carbon and treated with ethanolic hydrogen chloride to obtain ethyl 6,7-dimethoxy-4-(3,4-dimethoxyphenyl)-2-[4-(1-methylimidazol-2-yl)butyl]quinoline-3-carboxylate It was recrystallized from chloroform/ethyl acetate.

Pale yellow prisms. mp. 180–183° C. Elemental Analysis: Calcd. for $C_{30}H_{35}N_3O_6$.2HCl.$H_2O$: C,57.69; H,6.29; N,6.73 Found: C,57.48; H,6.09; N,6.60.

EXAMPLE 97

A mixture of ethyl 2-chloromethyl-6,7-dimethoxy-4-(3,4-dimethoxyphenyl)quinoline-3-carboxylate (1.5 g), 2-hydroxy-6-methylpyridine (0.4 g), potassium carbonate (0.511 g) and N,N-dimethylformamide (20 ml) was stirred at 120° C. for 2 hours. Then the mixture was poured into water and extracted with ethyl acetate. The ethyl acetate layer was washed with water and dried ($MgSO_4$), and the solvent was distilled off. The residual oil was subjected to column chromatography on silica gel. From the fraction eluted with ethyl acetate, ethyl 6,7-dimethoxy-4-(3,4-dimethoxyphenyl)- 2-[(2-methyl-6-pyridyl)oxymethyl]

quinoline-3-carboxylate (0.79 g, 46%) was obtained and recrystallized from chloroform/hexane.

Yellow prisms. mp. 173–174° C. Elemental Analysis: Calcd. for $C_{29}H_{30}N_2O_7$: C,67.17; H,5.83; N,5.40 Found: C,66.97; H,6.02; N,5.16.

EXAMPLE 98

A mixture of ethyl 2-iodomethyl-6,7-dimethoxy-4- (3,4-dimethoxyphenyl)quinoline-3-carboxylate (9.0 g), 2-hydroxy-1-methylimidazole (1.8 g), silver carbonate (I) ($Ag_2CO_3$) (5.1 g) and benzene (100 ml) was stirred at 50° C. for 18 hours. Then the insoluble materials were filtered off. The filtrate was washed with water, dried ($MgSO_4$), and the solvent was distilled off. The residual oil was subjected to column chromatography on silica gel. From the fraction eluted with chloroform/ethyl acetate (5:1, v/v), ethyl 6,7-dimethoxy-4-(3,4-dimethoxyphenyl)-2-[(1-methyl-2-imidazolyl)oxymethyl]quinoline-3-carboxylate (0.8 g, 9%) was obtained and recrystallized from ethyl acetate/hexane.

Colorless prisms. mp. 151–152° C. Elemental Analysis: Calcd. for $C_{27}H_{29}N_3O_7$: C,63.90; H,5.87; N,8.28 Found: C,63.74; H,5.87; N,7.99.

EXAMPLE 99

A mixture of ethyl 6,7-dimethoxy-4-(3,4-dimethoxyphenyl)-2-[(1-methylimidazol-2-yl)thiomethyl]quinoline-3-carboxylate (0.6 g), 2N NaOH (1.7 ml) and ethanol (12 ml) was refluxed for 6 hours. The reaction mixture was concentrated in vacuo. The residue was diluted with $H_2O$, washed with ethyl acetate, acidified with 2N HCl and extracted with ethyl acetate. The extract was washed with $H_2O$, dried over MgSO4, and concentrated in vacuo to give crystals. Recrystallization from ethanol-ethyl ether gave 6,7-dimethoxy-4-(3,4-dimethoxyphenyl)-2-[(1-methylimidazol-2-yl)thiomethyl]quinoline-3-carboxylic acid (0.3 g, 53%) as colorless prisms, mp 213–214° C.

Elemental Analysis: Calcd. for $C_{25}H_{25}N_3O_6S.1/2H_2O$: C,59.51; H,5.19; N,8.32 Found: C,59.38; H,5.40; N,7.93

What is claimed is:

1. A compound of the formula (I):

(I)

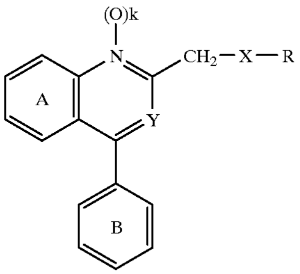

wherein Y is C—G, wherein G is carboxyl which may be esterified in which the esterified carboxyl group includes alkoxycarbonyl and aralkyoxycarbonyl; X is an optionally oxidized sulfur atom, or $—(CH_2)_q—$, wherein q is an integer of 1 to 5; R is an optionally substituted hydrocarbon group or optionally substituted heterocyclic group having a ring-constituting carbon atom attached to X, in which the hydrocarbon or heterocyclic group may be substituted with 1 to 3 substituents selected from the group consisting of $C_{1-6}$ alkyl, $C_{2-6}$ alkenyl, $C_{2-6}$ alkynyl, cycloalkyl, aryl, an aromatic monocyclic or condensed heterocyclic group and a saturated or unsaturated non-aromatic heterocyclic group each of which has at least one hetero atom selected from oxygen, sulfur and nitrogen, aralkyl, amino, N-monosubstituted amino, N,N disubstituted amino, amidino, acyl, carbamoyl, N-monosubstituted carbamoyl, N,N disubstituted carbamoyl, sulfamoyl, N-monosubstituted sulfamoyl, N,N disubstituted sulfamoyl, carboxyl, alkoxycarbonyl having $C_{1-6}$ alkoxy, hydroxyl, $C_{1-6}$ alkoxy, $C_{2-6}$ alkenyloxy, cycloalkyloxy, aralkyloxy, aryloxy, mercapto, $C_{1-6}$ alkylthio, aralkylthio, arylthio, sulfo, cyano, azido, nitro, nitroso and halogen; each of A ring and B ring may optionally have 1 to 4 substituents selected from the group consisting of halogen, nitro, straight-chain branched-chain or cyclic $C_{1-10}$ alkyl, hydroxyl, protected hydroxyl, thiol, protected thiol, amino, N-monosubstituted amino, N,N disubstituted amino, acyl, carboxyl, alkoxycarbonyl, aralkyloxycarbonyl and $C_{6-14}$ aromatic hydrocarbon group, or when the substituents of the ring A or the ring B are adjacent to each other, the adjacent alkyl or protected hydroxyl substituents may be joined together to form a ring of the formula $—(CH_2)_m—$ or $—O—(CH_2)_n—O—$ wherein m is 3 to 5 and n is 1 to 3; and k is 0 or 1, or a salt thereof, provided that R is other than an aliphatic chain hydrocarbon group or an aromatic hydrocarbon group when X is $—(CH_2)_q—$.

2. A compound according to claim 1 wherein R is an aliphatic chain saturated hydrocarbon group, aliphatic chain unsaturated hydrocarbon group, aliphatic cyclic hydrocarbon group or aromatic hydrocarbon group, or a salt thereof.

3. A compound according to claim 1 wherein X is $—(CH_2)_q—$, or a salt thereof.

4. A compound according to claim 3 wherein q is 1, or a salt thereof.

5. A compound according to claim 1 wherein G is $C_{1-6}$ alkyloxycarbonyl, or a salt thereof.

6. A compound according to claim 5 wherein G is ethoxycarbonyl, or a salt thereof.

7. A compound according to claim 1 wherein G is aryl-$C_{1-6}$ alkyloxycarbonyl or a salt thereof.

8. A compound according to claim 7 wherein the aryl is benzyl or phenethyl or a salt thereof.

9. A compound according to claim 1 wherein X is thio, sulfinyl or sulfonyl, or a salt thereof.

10. A compound according to claim 9 wherein X is thio, or a salt thereof.

11. A compound according to claim 1 wherein each of the A ring and B ring may independently be substituted with the same or different 1 to 4 substituents selected from the group consisting of a halogen atom, nitro, optionally substituted alkyl, hydroxyl, protected hydroxyl, thiol, protected thiol, optionally substituted amino, acyl, carboxyl, alkoxycarbonyl, aralkyloxycarbonyl and a $C_{6-14}$ aromatic hydrocarbon group, and the adjacent alkyl or protected hydroxyl substituents may be linked together to form the group of the formula: $—(CH_2)_m—$ or $—O—(CH_2)_n—O—$, respectively, wherein m is an integer of 3 to 5 and n is an integer of 1 to 3 which forms a ring.

12. A compound according to claim 11 wherein the protected hydroxyl of the substituent of the A ring is methoxy at the 6- or 7-position of the

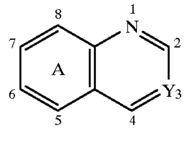

ring, or a salt thereof.

13. A compound according to claim 11 wherein the protected hydroxyl of the substituent of the B ring is methoxy or methylenedioxy, or a salt thereof.

14. A compound according to claim 13 wherein the methoxy is at the 3- or 4-position of the B ring, or a salt thereof.

15. A compound according to claim 1 wherein k is 0, or a salt thereof.

16. A compound according to claim 1, wherein A and B have one or two substituents and R is a heterocyclic group selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadizolyl, furazanyl, 1,3,4-thiadiazolyl, 1,2,3-triazolyl, 1,2,4-triazolyltetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzoimidazolyl, benzoxazolyl, 1,2-benzisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, pnenanthridinyl, phenanthrolinyl, indolizinyl, pyrrolo[1,2-b]pyridazinyl, pyrazolo[1,5-a]pyridyl, imidazo[1,2-a]pyridyl, imidazo[1,2-b]pyridaziyl, imidazo[1,2-a]pyriimidinyl, 1,2,4-triazolo[4,3-a]pyridyl, 1,2,4-triazolo[4,3-b]pyridyl, oxiranyl, azetidinyl, oxetanyl, thietanyl, pyrrolidinyl, tetrahydrofuryl, thiolanyl, piperidyl, tetrahydropyranyl, morpholinyl, thiomorpholinyl, and piperazinyl.

17. A compound according to claim 1 which is:

ethyl 6,7-dimethoxy-4-(3,4-dimethoxyphenyl)-2-[(1-methylimidazol-2-yl)sulfinylmethyl]quinoline-3-carboxylate, ethyl 6,7-dimethoxy-4-(4-methylphenyl)-2-[(1-methylimidazol-2-yl)thiomethyl]quinoline-3-carboxylate, ethyl 6,7-dimethoxy-4- (3,4-dimethoxyphenyl) -2-[(4-methyl- 1,2,4-triazol-3-yl)thiomethyl]quinoline-3-carboxylate, ethyl 6,7-dimethoxy-4-(3,4-dimethoxyphenyl)-2-[(1-methylimidazol-2-yl)thiomethyl]quinoline-3-carboxylate, ethyl 6,7-dimethoxy-4-(3,4-methylenedioxyphenyl)-2-[(1- methylimidazol-2-yl)thiomethyl]quinoline-3-carboxylate, ethyl 6,7-diethoxy-4-(3,4-dimethoxyphenyl)-2-[(1-methylimidazol-2-yl)thiomethyl]quinoline-3-carboxylate, ethyl 6,7-dimethoxy-4-(3,4-dimethoxyphenyl)-2-[2-(1-methylimidazol-2-yl)ethyl]quinoline-3-carboxylate, ethyl 2- [(2-benzimidazolyl) sulfinylmethyl]-6,7-dimethoxy-4- (3,4-dimethoxyphenyl)quinoline-3-carboxylate, ethyl 6,7-dimethoxy-4-(3,4-dimethoxyphenyl)-2-[(5-fluorobenzimidazol-2-yl)thiomethyl]quinoline-3-carboxylate, ethyl 6,7-dimethoxy-4-(3,4-dimethoxyphenyl)-2-[(benzothiazol-2-yl)thiomethyl]quinoline-3-carboxylate, ethyl 6,7-dimethoxy-4-(3,4-dimethoxyphenyl)-2-[(3,4-dihydro-4-oxoquinazolin-2-yl) thiomethyl]quinoline-3-carboxylate, ethyl 6,7-dimethoxy-4-(4-methoxyphenyl)-2-((benzimidazol-2- yl)thiomethyl]quinoline-3-carboxylate, ethyl 6,7-dimethoxy-4-(4-methoxyphenyl)-2-[(1-methylimidazol-2-yl)thiomethyl]quinoline-3-carboxylate, ethyl 6,7-dimethoxy-4-(3,4-dimethoxyphenyl)-2-[(4-chlorophenyl)thiomethyl]quinoline-3-carboxylate, ethyl 6,7-dimethoxy-4-(3,4-dimethoxyphenyl)-2-[(pyrido[1,2- a][1,3,4]triazol-5-yl)thiomethyl]quinoline-3-carboxylate, ethyl 6,7-dimethoxy-4-(3,4-dimethoxyphenyl)-2-[(4-chlorophenyl)methylthiomethyl]quinoline-3-carboxylate, ethyl 6,7-dimethoxy-4-(3,4-dimethoxyphenyl)-2-[(benzimidazol-2-yl)thiomethyl]quinoline-3-carboxylate, ethyl 6,7-dimethoxy-4-(3,4-dimethoxyphenyl)-2-[(6(1H)- pyrimidon-2-yl)thiomethyl]quinoline-3-carboxylate, ethyl 6,7-dimethoxy-4-(3,4-dimethyoxyphenyl)-2-[(3-hydroxypyridin-2-yl)thiomethyl]quinoline-3-carboxylate, or ethyl 6,7-dimethoxy-4-(3,4-dimethoxyphenyl)-2-[(2-thiazolin-2-yl)thiomethyl]quinoline-3-carboxylate.

18. An anti-inflammatory composition comprising an effective amount of a compound of the formula (I) as described in claim 1.

19. An anti-inflammatory composition according to claim 18, wherein X is $—(CH_2)q—$.

20. An anti-inflammatory composition according to claim 19, wherein q is 1.

21. An anti-inflammatory composition according to claim 18, wherein G is $C_{1-6}$ alkyloxycarbonyl.

22. An anti-inflammatory composition according to claim 21, wherein G is ethoxycarbonyl.

23. An anti-inflammatory composition according to claim 18, wherein X is thio, sulfinyl or sulfonyl.

24. An anti-inflammatory composition according to claim 23, wherein X is thio.

25. An anti-inflammatory composition according to claim 18, wherein each of the A ring and B ring may independently be substituted with the same or different 1 to 4 substituents selected from the group consisting of a halogen atom, nitro, optionally substituted alkyl, hydroxyl, protected hydroxyl, thiol, protected thiol, optionally substituted amino, acyl, carboxyl, alkoxycarbonyl, aralkyloxycarbonyl and a $C_{6-14}$ aromatic hydrocarbon group, and the adjacent alkyl or protected hydroxyl substituents may be linked together to form the group of the formula: $—CH_2)_m—$ or $—O—(CH_2)_n—O—$, respectively, wherein m is an integer of 3 to 5 and n is an integer of 1 to 3 which forms a ring.

26. An anti-inflammatory composition according to claim 25, wherein the protected hydroxy of the substituent of the A ring is methoxy at the 6- or 7-position of the quinoline ring.

27. An anti-inflammatory composition according to claim 25, wherein the protected hydroxy of the substituent of the B ring is methoxy or methylenedioxy.

28. An anti-inflammatory composition according to claim 27, wherein the methoxy is at the 3- or 4-position of the B ring.

29. An anti-inflammatory composition according to claim 18, wherein k is 1.

30. An anti-inflammatory composition according to claim 18, wherein the compound of the formula (I) is ethyl 6,7-dimethoxy-4-(3,4-dimethoxyphenyl)-2-[(1-methylimidazol-2-yl)sulfinylmethyl]quinoline-3-carboxylate, ethyl 6,7-dimethoxy-4-(4-methylphenyl)-2-[(1-methylimidazol-2-yl)thiomethyl]quinoline-3-carboxylate, ethyl 6,7-dimethoxy-4- (3,4-dimethoxyphenyl) -2-[(4-methyl- 1,2,4-triazol-3-yl)thiomethyl]quinoline-3-carboxylate, ethyl 6,7-dimethoxy-4-(3,4-dimethoxyphenyl)-2-[(1-methylimidazol-2-yl)thiomethyl]quinoline-3-carboxylate, ethyl 6,7-dimethoxy-4-(3,4-methylenedioxyphenyl)-2-[(1- methylimidazol-2-yl)thiomethyl]quinoline-3-carboxylate, ethyl 6,7-diethoxy-4-(3,4-dimethoxyphenyl)-2-[(1-methylimidazol-2-yl)thiomethyl]quinoline-3-carboxylate, ethyl 6,7-dimethoxy-4-(3,4-dimethoxyphenyl)-2-[(2-(1-methylimidazol-2-yl) ethyl]quinoline-3-carboxylate, ethyl 2-[(2-benzimidazolyl)sulfinylmethyl]-6,7-dimethoxy-4- (3,4-dimethoxyphenyl)quinoline-3-carboxylate, ethyl 6,7-dimethoxy-4-(3,4-dimethoxyphenyl)-2-[(5-fluorobenzimidazol-2-yl)thiomethyl]quinoline-3-carboxylate, ethyl 6,7-dimethoxy-4-(3,4-dimethoxyphenyl)-2-[(benzothiazol-2-yl)thiomethyl]quinoline-3-carboxylate, ethyl 6,7-dimethoxy-4-(3,4-dimethoxyphenyl)-2-[(3,4-dihydro-4-oxoquinazolin-2-yl)thiomethyl]quinoline-3-carboxylate, ethyl 6,7-dimethoxy-4-(4-methoxyphenyl)-2-[(benzimidazol-2- yl)thiomethyl]quinoline-3-carboxylate, ethyl 6,7-dimethoxy-4-(4-methoxyphenyl)-2-[(1-methylimidazol-2-yl)thiomethyl]quinoline-3-carboxylate, ethyl 6,7-dimethoxy-4-(3,4-dimethoxyphenyl)-2-[(4-chlorophenyl)thiomethyl]quinoline-3-carboxylate, ethyl 6,7-dimethoxy-4-(3,4-dimethoxyphenyl)-2-[(pyrido [1,2- a][1,3,4]triazol-5-yl)thiomethyl]quinoline-3-carboxylate, ethyl 6,7-dimethoxy-4-(3,4-dimethoxyphenyl)-2-[(4-chlorophenyl)methylthiomethyl]quinoline-3-carboxylate, ethyl 6,7-dimethoxy-4-(3,4-dimethoxyphenyl)-2-[(benzimidazol-2-yl)thiomethyl]quinoline-3-carboxylate, ethyl 6,7-dimethoxy-4-(3,4-dimethoxyphenyl)-2-[(6 (1H)- pyrimidon-2-yl)thiomethyl]quinoline-3-carboxylate, ethyl 6,7-dimethoxy-4-(3,4-dimethyoxyphenyl)-2-[(3-hydroxypyridin-2-yl)thiomethyl]quinoline-3-carboxylate, or ethyl 6,7-dimethoxy-4-(3,4-dimethoxyphenyl)-2-[(2-thiazolin-2-yl)thiomethyl]quinoline-3-carboxylate.

31. An anti-inflammatory composition according to claim 18, which is an agent for inhibiting arthrosis destruction.

32. An anti-inflammatory composition according to claim 18, which is an anti-rheumatism agent.

33. An anti-inflammatory composition according to claim 18, which is anti-chronic rheumatism agent.

34. An anti-inflammatory composition comprising an effective amount of a compound of the formula (I):

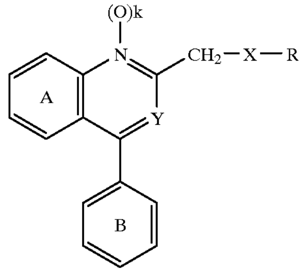

(I)

wherein Y is a nitrogen atom or C—G wherein G is carboxyl which may be esterified in which the esterified carboxyl group includes alkoxycarbonyl and aralkyoxycarbonyl; X is an optionally oxidized sulfur atom, or $—(CH_2)_q—$, wherein q is an integer of 1 to 5; R is an optionally substituted hydrocarbon group or optionally substituted heterocyclic group having a ring-constituting carbon atom attached to X, in which the hydrocarbon or heterocyclic group may be substituted with 1 to 3 substituents selected from the group consisting of $C_{1-6}$ alkyl, $C_{2-6}$ alkenyl, $C_{2-6}$ alkynyl, cycloalkyl, aryl, an aromatic monocyclic or condensed heterocyclic group and a saturated or unsaturated nonaromatic heterocyclic group each of which has at least one hetero atom selected from oxygen, sulfur and nitrogen, aralkyl, amino, N-monosubstituted amino, N,N-disubstituted amino, amidino, acyl, carbamoyl, N-monosubstituted carbamoyl, N,N disubstituted carbamoyl, sulfamoyl, N-monosubstituted sulfamoyl, N,N disubstituted sulfamoyl, carboxyl, alkoxycarbonyl having $C_{1-6}$ alkoxy, hydroxyl, $C_{1-6}$ alkoxy, $C_{2-6}$ alkenyloxy, cycloalkyloxy, aralkyloxy, aryloxy, mercapto, $C_{1-6}$ alkylthio, aralkylthio, arylthio, sulfo, cyano, azido, nitro, nitroso and halogen; each of A ring and B ring may optionally have 1 to 4 substituents selected from the group consisting of halogen, nitro, straight-chain, branched-chain or cyclic $C_{1-10}$ alkyl, hydroxyl, protected hydroxyl, thiol, protected thiol, amino, N-monosubstituted amino, N,N disubstituted amino, acyl, carboxyl, alkoxycarbonyl, aralkyloxycarbonyl and $C_{6-14}$ aromatic hydrocarbon group, or when the substituents of the ring A or the ring B are adjacent to each other, the adjacent alkyl or protected hydroxyl substituents may be joined together to form a ring of the formula $—(CH_2)_m—$ or $—O—(CH_2)_n—O—$, wherein m is 3 to 5 and n is 1 to 3; and k is 0 or 1, provided that R is other than an optionally substituted aliphatic chain hydrocarbon group when X is a sulfur atom and Y is a nitrogen atom, and provided that R is other than an aliphatic chain hydrocarbon group or an aromatic hydrocarbon group when X is $—(CH_2)_q—$, or a pharmaceutically acceptable salt thereof, with a pharmaceutically acceptable carrier therefor.

35. An anti-inflammatory composition according to claim 34 wherein X is $—(CH_2)_q—$.

36. An anti-inflammatory composition according to claim 34 wherein Y is C—G and G is $C_{1-6}$ alkyloxycarbonyl.

37. An anti-inflammatory composition according to claim 36, wherein G is ethoxycarbonyl.

38. An anti-inflammatory composition according to claim 34, wherein each of the A ring and B ring may independently be substituted with the same or different 1 to 4 substituents selected from the group consisting of a halogen atom, nitro, optionally substituted alkyl, hydroxyl, protected hydroxyl, thiol, protected thiol, optionally substituted amino, acyl, carboxyl, alkoxycarbonyl, aralkyloxycarbonyl and a $C_{6-14}$ aromatic hydrocarbon group, and the adjacent alkyl or protected hydroxyl substituents may be linked together to form the group of the formula: —$(CH_2)_m$— or —O—$(CH_2)_n$—O—, respectively wherein m is an integer of 3 to 5 and n is an integer of 1 to 3 which forms a ring.

39. An anti-inflammatory composition according to claim 38, wherein the protected hydroxyl of the substituent of the A ring is methoxy at the 6- or 7-position of the quinoline ring.

40. An anti-inflammatory composition according to claim 38, wherein the protected hydroxyl of the substituent of the B ring is methoxy or methylenedioxy.

41. An anti-inflammatory composition according to claim 34, wherein the methoxy is at the 3- or 4-position of the B ring.

42. An anti-inflammatory composition according to claim 34 which is an agent for inhibiting arthrosis destruction.

43. An anti-inflammatory composition according to claim 34 which is an antirheumatic agent.

44. An antiinflammatory composition according to claim 34, wherein A and B have one or two substituents and R is a heterocyclic group selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadizolyl, furazanyl, 1,3,4-thiadiazolyl, 1,2,3-triazolyl, 1,2,4-triazolyl tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzoimidazolyl, benzoxazolyl, 1,2-benzisoxazolyl, benzothiazolyl,1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, pnenanthridinyl, phenanthrolinyl, indolizinyl, pyrrolo[1,2-b]pyridazinyl, pyrazolo[1,5-a]pyridyl, imidazo[1,2-a]pyridyl, imidazo[1,2-b]pyridaziyl, imidazo[1,2-a]pyriimidinyl, 1,2,4-triazolo[4,3-a]pyridyl, 1,2,4-triazolo[4,3-b]pyridyl, oxiranyl, azetidinyl, oxetanyl, thietanyl, pyrrolidinyl, tetrahydrofuryl, thiolanyl, piperidyl, tetrahydropyranyl, morpholinyl, thiomorpholinyl, and piperazinyl.

45. An anti-inflammatory composition according to claim 34, wherein X is thio, sulfinyl or sulfonyl.

46. An anti-inflammatory composition according to claim 45, wherein X is thio.

47. An anti-inflammatory composition according to claim 34, wherein q is 1.

48. An anti-inflammatory composition according to claim 34, wherein k is 1.

49. An anti-inflammatory composition according to claim 34, wherein the compound of the formula (I) is:

ethyl 6,7-dimethoxy-4-(3,4-dimethoxyphenyl)-2-[(1-methylimidazol-2-yl)sulfinylmethyl]quinoline-3-carboxylate, ethyl 6,7-dimethoxy-4-(4-methylphenyl)-2-[(1-methylimidazol-2-yl)thiomethyl]quinoline-3-carboxylate, ethyl 6,7-dimethoxy-4-(3,4-dimethoxyphenyl)-2-[(4-methyl- 1,2,4-triazol-3-yl)thiomethyl]quinoline-3-carboxylate, ethyl 6,7-dimethoxy-4-(3,4-dimethoxyphenyl)-2-[(1-methylimidazol-2-yl)thiomethyl]quinoline-3-carboxylate, ethyl 6,7-dimethoxy-4-(3,4-methylenedioxyphenyl)-2-[(1- methylimidazol-2-yl)thiomethyl]quinoline-3-carboxylate, ethyl 6,7-diethoxy-4-(3,4-dimethoxyphenyl)-2-[(1-methylimidazol-2-yl)thiomethyl]quinoline-3-carboxylate, ethyl 6,7-dimethoxy-4-(3,4-dimethoxyphenyl)-2-[2-(1-methylimidazol-2-yl)ethyl]quinoline-3-carboxylate, ethyl2-[(2-benzimidazolyl)sulfinylmethyl]-6,7-dimethoxy-4- (3,4-dimethoxyphenyl)quinoline-3-carboxylate, ethyl 6,7-dimethoxy-4-(3,4-dimethoxyphenyl)-2-[(5-fluorobenzimidazol-2-yl)thiomethyl]quinoline-3-carboxylate, ethyl 6,7-dimethoxy-4-(3,4-dimethoxyphenyl)-2-[(benzothiazol-2-yl)thiomethyl]quinoline-3-carboxylate, ethyl 6,7-dimethoxy-4-(3,4-dimethoxyphenyl)-2-[(3,4-dihydro-4-oxoquinazolin-2-yl)thiomethyl]quinoline-3-carboxylate, ethyl 6,7-dimethoxy-4-(4-methoxyphenyl)-2-[(benzimidazol-2- yl)thiomethyl]quinoline-3-carboxylate, ethyl 6,7-dimethoxy-4-(4-methoxyphenyl)-2-[(1-methylimidazol-2-yl)thiomethyl]quinoline-3-carboxylate, ethyl 6,7-dimethoxy-4-(3,4-dimethoxyphenyl)-2-[(4-chlorophenyl)thiomethyl]quinoline-3-carboxylate, ethyl 6,7-dimethoxy-4-(3,4-dimethoxyphenyl)-2-[(pyrido[1,2- a][1,3,4]triazol-5-yl)thiomethyl]quinoline-3-carboxylate, ethyl 6,7-dimethoxy-4-(3,4-dimethoxyphenyl)-2-[(4-chlorophenyl)methylthiomethyl]quinoline-3-carboxylate, ethyl 6,7-dimethoxy-4-(3,4-dimethoxyphenyl)-2-[(benzimidazol-2-yl)thiomethyl]quinoline-3-carboxylate, ethyl 6,7-dimethoxy-4-(3,4-dimethoxyphenyl)-2-[(6(1H)- pyrimidon-2-yl)thiomethyl]quinoline-3-carboxylate, ethyl 6,7-dimethoxy-4-(3,4-dimethyoxyphenyl)-2-[(3-hydroxypyridin-2-yl)thiomethyl]quinoline-3-carboxylate, or ethyl 6,7-dimethoxy-4-(3,4-dimethoxyphenyl)-2-[(2-thiazolin-2-yl)thiomethyl]quinoline-3-carboxylate.

50. An anti-inflammatory composition according to claim 34, which is an anti-chronic rheumatism agent.

51. A process for producing a compound of the formula (I-1):

(I-1)

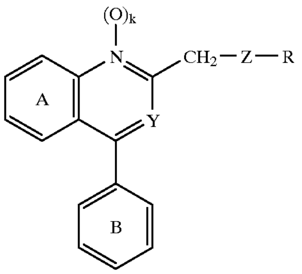

wherein Z is an optionally oxidized sulfur atom and Y is C—G, wherein G is carboxyl which may be esterified in which the esterified carboxyl group includes alkoxycarbonyl and aralkyoxycarbonyl; R is an optionally substituted hydrocarbon group or optionally substituted heterocyclic group having a ring-constituting carbon atom attached to Z, in which the hydrocarbon or heterocyclic group may be substituted with 1 to 3 substitutents selected from the group consisting of $C_{1-6}$ alkyl, $C_{2-6}$ alkenyl, $C_{2-6}$ alkynyl, cycloalkyl, aryl, an aromatic monocyclic or condensed heterocyclic group each of which has at least one hetero atom selected from oxygen, sulfur and nitrogen, aralkyl, amino, N-monosubstituted amino, N,N disubstituted amino, amidino, acyl, carbamoyl, N-monosubstituted carbamoyl, N,N disubstituted carbamoyl, sulfamoyl, N-monosubstituted sulfamoyl, N,N disubstituted sulfamoyl, carboxyl, alkoxycarbonyl having $C_{1-6}$ alkoxy, $C_{2-6}$alkenyloxy, cycloalkyloxy, aralkyloxy, aryloxy, mercapto, $C_{1-6}$ alkylthio, aralkylthio, arylthio, sulfo, cyano, azido, nitro, nitroso and halogen; each selected from the group consisting of halogen, nitro, straight-chain, branched-chain or cyclic $C_{1-10}$ hydroxyl, protected hydroxyl, thiol, protected thiol, amino, N-monosubstituted amino, N,N disubstituted amino, acyl, carboxyl, alkyoxycarbonyl, aralkoxycarbonyl and $C_{6-14}$ aromatic hydrocarbon group, or when the substitutents of the ring A or the ring B are adjacent to each other, the adjacent alkyl or protected hydroxyl substituents may be joined together to form a ring of the formula $-(CH_2)_m-$ or $-O-(CH_2)_n-O$ wherein m is 3 to 5 and n is 1 to 3; k is 0 or 1, or a salt thereof, which comprises reacting a compound of the formula (II):

(II)

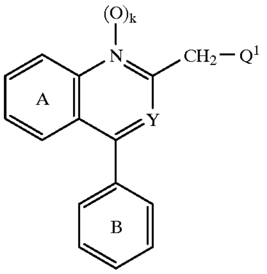

wherein $Q^1$ is a leaving group and the other symbols are as defined above, or a salt thereof with a compound of the formula (III):

R—SH (III)

wherein R is as defined above, and, if necessary, subjecting the resultant to oxidation.

52. A process according to claim 51 wherein $Q^1$ is halogen, or hydroxyl activated by esterification with an organic sulfonic acid or organic phosphoric acid.

53. A process according to claim 52 wherein $Q^1$ is chlorine, bromine, iodine, p-toluenesulfonyloxy, methanesulfonyloxy, diphenylphosphoryloxy, dibenzylphosphoryloxy or dimethylphosphoryloxy.

54. A process according claim 53 wherein $Q^1$ is chlorine or bromine.

55. A process for producing a compound of the formula (I-2):

(I-2)

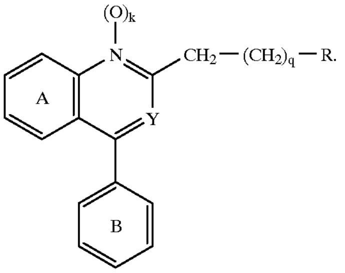

Wherein q is an integer of 1 to 5 and Y is C—G, wherein G is carboxyl which may be esterified in which the esterified carboxyl group includes alkoxycarbonyl and aralkyoxycarbonyl; R is an optionally substituted hydrocarbon group or optionally substituted heterocyclic group having a ring-constituting carbon atom attached to X, in which the hydrocarbon or heterocyclic group may be substituted with 1 to 3 substitutents selected from the group consisting of $C_{1-6}$ alkyl, $C_{2-6}$ alkenyl, $C_{2-6}$ alkynyl, cycloalkyl, aryl, an aromatic monocyclic or condensed heterocyclic group each of which has at least one hetero atom selected from oxygen, sulfur and nitrogen, aralkyl, amino, N-monosubstituted amino, N,N disubstituted amino, amidino, acyl, carbamoyl, N-monosubstituted carbamoyl, N,N disubstituted carbamoyl, sulfamoyl, N-monosubstituted sulfamoyl, N,N disubstituted sulfamoyl, carboxyl, alkoxycarbonyl having $C_{1-6}$ alkoxy, $C_{2-6}$ alkenyloxy, cycloalkyloxy, aralkyloxy, aryloxy, mercapto, $C_{1-6}$ alkylthio, aralkylthio, arylthio, sulfo, cyano, azido, nitro, nitroso and halogen; each selected from the group consisting of halogen, nitro, straight-chain, branched-chain or cyclic $C_{1-10}$ alkyl, hydroxyl, protected hydroxyl, thiol, protected thiol, amino, N-monosubstituted amino, N,N disubstituted amino, acyl, carboxyl, alkyoxycarbonyl, aralkoxycarbonyl and $C_{6-14}$ aromatic hydrocarbon group, or when the substitutents of the ring A or the ring B are adjacent to each other, the adjacent alkyl or protected hydroxyl substituents may be joined together to form a ring of the formula $-(CH_2)_m-$ or $-O-(CH_2)_n-O$ wherein m is 3 to 5 and n is 1 to 3; k is 0 or 1, provided that R is other than an aliphatic chain hydrocarbon group or an aromatic hydrocarbon group when, or a salt thereof, which comprises reacting a compound of the formula (IV):

(IV)

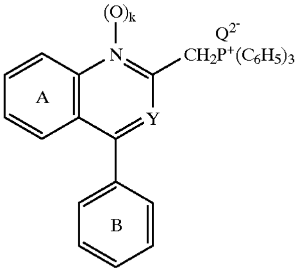

wherein Q is a halogen atom and the other symbols are as defined above, with the compound of the formula (V):

$R-(CH_2)_{q-1}-CHO$ (V)

wherein the symbols are as defined above, and subjecting the resultant to reduction.

56. A process according to claim 55 wherein R is an aliphatic chain unsaturated hydrocarbon group, aliphatic cyclic hydrocarbon group or aromatic hydrocarbon group.

57. A process according to claim 55 wherein R is an aromatic heterocyclic group or non-aromatic heterocyclic group.

58. A process according to claim 55 wherein $Q^2$ is chlorine or bromine.

59. A method of treating inflammation in a mammal which comprises administering to a mammal in need thereof an effective amount of compound of the formula (I):

(I)

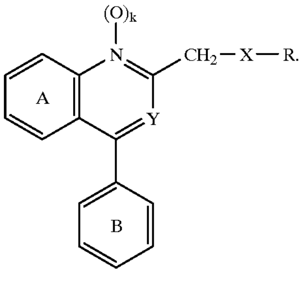

Wherein Y is a nitrogen atom or C—G, wherein G is carboxyl which may be esterified; X is an optionally oxidized sulfur atom, an oxygen atom or $—(CH_2)_q—$, wherein q is an integer of 1 to 5; R is an optionally substituted hydrocarbon group or optionally substituted heterocyclic group having a carbon atom attached to X; each of A ring and B ring may optionally have at least one substituent, and k is 0 or 1; or a salt thereof.

60. A method according to claim 59, wherein X is $—(CH_2)q—$.

61. A method according to claim 55, wherein X is thio, sulfinyl, or sulfonyl.

62. A method according to claim 61, wherein X is thio.

63. A method according to claim 59, wherein q is 1.

64. A method according to claim 59, wherein Y is C—G and G is $C_{1-6}$ alkyloxycarbonyl.

65. A method according to claim 64, wherein G is ethoxycarbonyl.

66. A method according to claim 59, wherein each of the A ring and B ring may independently be substituted with the same or different 1 to 4 substituents selected from the group consisting of a halogen atom, nitro, optionally substituted alkyl, hydroxyl, protected hydroxyl, thiol, protected thiol, optionally substituted amino, acyl, carboxyl, alkoxycarbonyl, aralkyloxycarbonyl and a $C_{6-14}$ aromatic hydrocarbon group, and the adjacent alkyl or protected hydroxyl substituents may be linked together to form the group of the formula: $—(CH_2)_m—$ or $—O—(CH_2)_n—O—$, respectively, wherein m is an integer of 3 to 5 and n is an integer of 1 to 3 which forms a ring.

67. A method according to claim 66 wherein the substituent of the A ring is methoxy at the 6- or 7-position of the

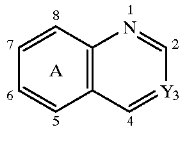

ring.

68. A method according to claim 66, wherein the substituent of the B ring is methoxy or methylenedioxy.

69. A method according to claim 66, wherein the protected hydroxyl is methoxy and the methoxy is at the 3- or 4-position of the B ring.

70. A method according to claim 59, wherein k is 1.

71. A method according to claim 59, wherein the compound of the formula (I) is:

ethyl 6,7-dimethoxy-4-(3,4-dimethoxyphenyl)-2-[(1-methylimidazol-2-yl)sulfinylmethyl]quinoline-3-carboxylate, ethyl 6,7-dimethoxy-4-(4-methylphenyl)-2-[(1-methylimidazol-2-yl)thiomethyl]quinoline-3-carboxylate, ethyl 6,7-dimethoxy-4-(3,4-dimethoxyphenyl)-2-[(4-methyl- 1,2,4-triazol-3-yl)thiomethyl]quinoline-3-carboxylate, ethyl 6,7-dimethoxy-4-(3,4-dimethoxyphenyl)-2-[(1-methylimidazol-2-yl)thiomethyl]quinoline-3-carboxylate, ethyl 6,7-dimethoxy-4-(3,4-methylenedioxyphenyl)-2-[(1- methylimidazol-2-yl)thiomethyl]quinoline-3-carboxylate, ethyl 6,7-diethoxy-4-(3,4-dimethoxyphenyl)-2-[(1-methylimidazol-2-yl)thiomethyl]quinoline-3-carboxylate, ethyl 6,7-dimethoxy-4-(3,4-dimethoxyphenyl)-2-[2-(1-methylimidazol-2-yl)ethyl]quinoline-3-carboxylate, ethyl 2-[(2-benzimidazolyl)sulfinylmethyl]-6,7-dimethoxy-4- (3,4-dimethoxyphenyl)quinoline-3-carboxylate, ethyl 6,7-dimethoxy-4-(3,4-dimethoxyphenyl)-2-[(5-fluorobenzimidazol-2-yl)thiomethyl]quinoline-3-carboxylate, ethyl 6,7-dimethoxy-4-(3,4-dimethoxyphenyl)-2-[(benzothiazol-2-yl)thiomethyl]quinoline-3-carboxylate, ethyl 6,7-dimethoxy-4-(3,4-dimethoxyphenyl)-2-[(3,4-dihydro-4-oxoquinazolin-2-yl) thiomethyl]quinoline-3-carboxylate, ethyl 6,7-dimethoxy-4-(4-methoxyphenyl)-2-[(benzimidazol-2- yl)thiomethyl]quinoline-3-carboxylate, ethyl 6,7-dimethoxy-4-(4-methoxyphenyl)-2-[(1-methylimidazol-2-yl)thiomethyl]quinoline-3-carboxylate, ethyl 6,7-dimethoxy-4-(3,4-dimethoxyphenyl)-2-[(4-chlorophenyl)thiomethyl]quinoline-3-carboxylate, ethyl 6,7-dimethoxy-4-(3,4-dimethoxyphenyl) -2-[(pyrido[1,2- a][1,3,4]triazol-5-yl)thiomethyl] quinoline-3-carboxylate, ethyl 6,7-dimethoxy-4-(3,4-dimethoxyphenyl)-2-[(4-chlorophenyl)methylthiomethyl]quinoline-3-carboxylate, ethyl 6,7-dimethoxy-4-(3,4-dimethoxyphenyl)-2-[(benzimidazol-2-yl)thiomethyl]quinoline-3-carboxylate, ethyl 6,7-dimethoxy-4-(3,4-dimethoxyphenyl)-2-[(6(1H)- pyrimidon-2-yl)thiomethyl]quinoline-3-carboxylate, ethyl 6,7-dimethoxy-4-(3,4-dimethyoxyphenyl)-2-[(3-hydroxypyridin-2-yl)thiomethyl]quinoline-3-carboxylate, or ethyl 6,7-dimethoxy-4-(3,4-dimethoxyphenyl)-2-[(2-thiazolin-2-yl)thiomethyl]quinoline-3-carboxylate.

72. A method according to claim 59, wherein the inflammation is arthrosis destruction.

73. A method according to claim 59, wherein the inflammation is rheumatism.

74. A method according to claim 59, wherein the inflammation is chronic rheumatism.

* * * * *

UNITED STATES PATENT AND TRADEMARK OFFICE

CERTIFICATE OF CORRECTION

PATENT NO. : 5,948,782

DATED : September 7, 1999

INVENTOR(S) : Takashi SOHDA et al.

It is certified that error appears in the above-identified patent and that said Letters Patent is hereby corrected as shown below:

On the title page, item

[30] Foreign Application Priority Data, contains a typographical error wherein "4-037952" should read --5-037952--;

Signed and Sealed this

Thirtieth Day of May, 2000

Attest:

Q. TODD DICKINSON

Attesting Officer

*Director of Patents and Trademarks*